(12) United States Patent
Shaw et al.

(10) Patent No.: US 7,052,879 B2
(45) Date of Patent: May 30, 2006

(54) **RECOMBINANT *CANDIDA RUGOSA* LIPASES**

(75) Inventors: Jei-Fu Shaw, Taipei (TW); Guan-Chiun Lee, Taipei (TW); Shye-Jye Tang, Taipei (TW)

(73) Assignee: Academia Sinica, Taipei (TW)

( * ) Notice: Subject to any disclaimer, the term of this patent is extended or adjusted under 35 U.S.C. 154(b) by 602 days.

(21) Appl. No.: 09/943,857

(22) Filed: Aug. 31, 2001

(65) Prior Publication Data

US 2003/0124701 A1   Jul. 3, 2003

(51) Int. Cl.
C12P 19/34 (2006.01)
C07H 21/04 (2006.01)

(52) U.S. Cl. .............................. 435/91.2; 435/254.23; 435/252.3; 435/254.2; 435/252.33; 536/23.2

(58) Field of Classification Search ........ 435/195–198, 435/252.33, 254.11, 320.1, 91.4; 536/23.1, 536/23.2
See application file for complete search history.

(56) References Cited

FOREIGN PATENT DOCUMENTS

WO    WO 99/14338    3/1999

OTHER PUBLICATIONS

Lilia Alberghina, et al. *Cloning, Sequencing, and Expression of Candida rugosa Lipases*. Methods in Enzymology 284:246-260, 1997. XP002067443.

Stefania Brocca, et al. *Design, Total Synthesis, and functional overexpression of the Candida rugosa lip1 gene coding for a major industrial lipase*. Protein Science 7(6):1415-1422, 1998. XP00929163.

Yoshiyuki Kawaguchi, et al. *The codon CUG is read as serine in an asporogenic yeast Candida cylindracea*. Nature 341(6238):164-166, Sep. 1989. XP000084053.

Shye-Jye Tang, et al. *Recombinant Expression of the Candida rugosa lip4 Lipase in Escherichia coli*. Protein Expression and Purification 20:308-313, 2000. XP002204904.

Guan-Chiun Lee, Shye-Jye Tang. Kuang-Hui Sun, Jei-Fu Shaw. *Analysis of the Gene Family Encoding Lipases in Candida rugosa by Competitive Reverse Transcription-PCR*. Applied and Environmental Microbiology, vol. 65, No. 9, Sep. 1999, pp. 3888-3895.

Shye-Jye Tang, Jei-Fu Shaw, Kuang-Hui Sun, Guang-Huan Sun, Terng-Yuan Chang, Ching-Kai Lin, Yuh-Chih Lo, and Guang-Chiun Lee. *Recombinant Expression and Characterization of the Candida rugosa lip4 Lipase in Pichia pastoris: Comparison of Glycosylation. Activity, and Stability*. Archives of Biochemistry and Biophysics. vol. 387, No. 1, Mar. 2001, pp. 93-98.

Rey-Chang Chang, Shu-Jen Chou, Jei-Fu Shaw. *Multiple forms and functions of Candida rugosa lipase*. Biotechnol. Appl. Biochem. vol. 19, 1994, pp. 93-97.

Liming Ge and Peter Rudolph. *Simultaneous Introduction of Multiple Mutations Using Overlap Extension PCR*. Biotechniques, vol. 22, No. 1, Jan. 1997, pp. 28-30.

Miroslaw Cygler and Joseph D. Schrag. *Structure and conformational flexibility of Candida rugosa lipase*. Biochimica et Biophysica Acta, vol. 1441, 1999. pp. 205-214.

Lilia Alberghina et al. "Protein Engineering of a Fungal Lipase". Engineering with Lipases, Kluwer Academia Publishers, Netherlands, pp. 219-228, XP-002067509.

Marina Lotti et al. "Cloning and Analysis of *Candida cylindracea* lipase sequences". Gene 124(1):45-55, 1993. XP-001084201.

Longhi et al. "Lipase I precursor (EC 3.1.1.3) (LIP1)". Database Accession No. P20261-XP-002230351.

*Primary Examiner*—Nashaat T. Nashed
(74) *Attorney, Agent, or Firm*—Fish & Richardson P.C.

(57) ABSTRACT

The present invention features an isolated nucleic acid that includes a mutant DNA encoding a *Candida rugosa* lipase, wherein the mutant DNA is 80% identical to a wild-type DNA encoding the *Candida rugosa* lipase, and includes at least 12 (e.g., 13, 15, 17, or all) universal serine codons corresponding to CTG codons in the wild-type DNA. Each of the universal serine codons, independently, is TCT, TCC, TCA, TCG, AGT, or AGC. The *Candida rugosa* lipase can be *Candida rugosa* lipase 1, 2, 3, 4, 5, or 8.

22 Claims, No Drawings

RECOMBINANT *CANDIDA RUGOSA* LIPASES

BACKGROUND

Lipase (EC 3.1.1.3) is able to catalyze a wide range of chemical reactions, which include nonspecific and stereo-specific hydrolysis, esterfication, trans-esterification, and interesterification. In addition, it catalyzes the hydrolysis of an ester bond at water-lipid interface. See, e.g., Ader et al. (1997) *Methods Enzymot.* 286: 351–385; Gandhi (1997) *J Am Oil Chem. Soc.* 74: 621–634; Klibanov (1990) *Acc. Chem. Res.* 23: 114–120; Shaw et al. (1990) *Biotechnol. Bioeng.* 35: 132–137; and Wang et al. (1988) *Biotechnol. Bioeng.* 31: 628–633.

Due to its catalytic abilities, a *Candida rugosa* lipase, among commercial lipases, is widely used in bioindustries. Generally, crude *C. rugosa* lipases are applied in almost all biocatalytic applications, however, enzymes from various suppliers have been reported to show variations in their catalytic efficiency and stereospecificity. See Barton et al. (1990) *Enzyme Microb. Technol.* 12: 577–583. Several lipase isomers (i.e., isozymes) have been isolated from the crude *C. rugosa* lipase, and the lipase isozymes were shown to be different in catalytic efficiency and specificity. See Shaw et al. (1989) *Biotechnol. Lett.* 11: 779–784; Rúa et al. (1993) *Biochem. Biophysl Acta* 1156: 181–189; Diczfalusy et al. (1997) *Arch. Biochem. Biophys.* 348: 1–8.

To date, five lipase-encoding genomic sequences from *C. rugosa* have been characterized. See, for example, Longhi et al. (1992) *Biochim. Biophy. Acta* 1131: 227–232; and Lotti et al. (1993) *Gene* 124: 45–55. The five lipase-encoding genes (LIP1, 2, 3, 4, and 5) have been isolated from a SacI genomic library of the yeast *C. rugosa* by colony hybridization. The five genes encode for mature proteins of 534 residues with putative signal peptides of 15 (in LIP1, 3, 4, and 5) and 14 (in LIP 2) amino acids in length, respectively. The five deduced amino acid sequences share an overall identity of 66% and similarity of 84%. Due to a high sequence homology among the five deduced amino acid sequences and the differential expression level of the five lipase genes (Lee et al. (1999) *Appl. Environ. Microbiol.* 65: 3888–3895), it is difficult to purify each isozyme directly from the cultures of *C. rugosa* on a preparative scale for industrial applications.

Further, although these isozymes are conserved at a catalytic triad (including amino acids S209, H449, and E341) and at the sites involved in disulfide bonds formation (including amino acids C60, C97 and C268, C277), they differ in N-glycosylation sites, isoelectric points, and some other features in their hydrophobic profiles. In addition, each of the isozymes may account for certain properties, such as catalytic efficiency and specificity. See Chang et al. (1994) *Biotechnol. Appl. Biochem.* 19: 93–97. Accordingly, cloning and functional expression of a *C. rugosa* lipase isozyme are desirable for producing a pure isozyme with certain properties for industrial applications.

However, *C. rugosa* is a dimorphic yeast in which the triplet CTG, a universal codon for leucine, is read as serine. As a result, the functional expression of a *C. rugosa* isozyme becomes unfeasible in a common host cell (in which CTG is read as leucine). See Kawaguchi et al. (1989) *Nature* 341: 164–166.

SUMMARY

This invention relates to a nucleic acid that can be used to functionally express a heterologous *C. rugosa* lipase in a common host cell.

In one aspect, the present invention features an isolated nucleic acid that includes a mutant DNA encoding a *C. rugosa* lipase. The mutant DNA is at least 80% (e.g., at least 85%, 90%, or 95%) identical to a wild-type DNA encoding the *C. rugosa* lipase, and includes at least 12 (e.g., 13, 15, 17, or all) universal serine codons corresponding to CTG codons in the wild-type DNA. Each of the CTG codon is read as serine in *C. rugosa*. Each of the universal serine codons, independently, is TCT, TCC, TCA, TCG, AGT, or AGC. The term "*C. rugosa* lipase" as used herein refers to a pure isozyme, and includes native *C. rugosa* lipases 1, 2, 3, 4, 5, and 8, as well as their variants. Examples of the just-described isolated nucleic acid include, but are not limited to, SEQ ID NOs:1, 3, 5, 7, and 9, the corresponding amino acid sequences of which are SEQ ID NOs:2, 4, 6, 8, and 10, respectively.

The mutant DNA can be a DNA of SEQ ID NO:1, 3, 5, 7, or 9, or a degenerate variant thereof. The degenerate variant refers to any other DNA sequence which encodes, based on universal codons, the same polypeptide as that encoded by the SEQ ID NO:1, 3, 5, 7, or 9. The mutant DNA can also be a DNA encoding a polypeptide sequence that is at least 90% (e.g., 95%, 98% or 100%) identical to the amino acid sequence of SEQ ID NO:2, 4, 6, 8, or 10. Indeed, the polypeptide sequence need not be a full length of the just-described amino acid sequence as long as its intended catalytic ability in the polypeptide has not been completely abolished. For example, a mutant DNA is a functional fragment containing at least 1070 nucleotides (e.g., 1200, or 1500 nucleotides) of the nucleotide sequence of SEQ ID NO:1, 3, 5, 7, or 9; or a sequence encoding a functional fragment of a polypeptide containing the amino acid sequence of SEQ ID NO:2, 4, 6, 8, or 10, wherein the fragment includes at least 350 amino acids (e.g., 400, or 500 amino acids).

The term "isolated nucleic acid" refers to a nucleic acid the structure of which is not identical to that of any naturally occurring nucleic acid or to that of any fragment of a naturally occurring genomic nucleic acid spanning more than three separate genes. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The above-described isolated nucleic acid of this invention can be introduced into and expressed in a microorganism, which is also within the scope of this invention. An example of the microorganism is a bacterium (e.g., *Escherichia coli*) or yeast (e.g., *Pichia pastoris*).

The "percent identity" (or "percent homology") of two amino acid sequences or of two nucleic acids can be determined using the algorithm of Thompson et al. (CLUSTAL W, 1994 Nucleic Acids Res. 22: 4673–4680). An amino acid sequence or a nucleotide sequence can also be used as a "query sequence" to perform a search against public databases to, for example, identify related sequences. Such searches can be performed using the algorithm of Karlin and Altschul (1990 Proc. Natl. Acad. Sci. USA 87: 2264–2268), modified as in Karlin and Altschul (1993 Proc. Natl Acad. Sci. USA 90: 5873–5877). Such an algorithm is incorporated into the NBLAST and XBLAST programs of Altschul et al. (1990 J Mol. Biol. 215: 403–410). BLAST nucleotide searches are performed with the NBLAST program, score =100, wordlength=12. BLAST protein searches are performed with the XBLAST program, score=50, wordlength=3. Where gaps exist between two sequences, Gapped BLAST is utilized as described in Altschul et al. (1997 Nucleic Acids Res. 25: 3389–3402). When utilizing BLAST and Gapped BLAST programs, the default parameters of the respective programs (e.g., XBLAST and NBLAST) are used. See www.ncbi.nlm.nih.gov/.

In another aspect, this invention features a method for preparing a mutant DNA encoding a *C. rugosa* lipase. The method includes providing a wild-type DNA encoding a *C. rugosa* lipase; and conducting PCR amplification by mixing the wild-type DNA, a DNA polymerase, a pair of external primers encompassing the entirety of the wild-type DNA, and a number of pairs of internal primers respectively encompassing fragments of the wild-type DNA. An "external primer" is a PCR primer designed to amplify the entirety of a mutant DNA and an "internal primer" is a PCR primer designed to amplify a fragment of the mutant DNA.; a primer can operate both as an external and as an internal primer. Each of the internal primers includes one or more of universal codons and anticodons for serine selected from TCT, TCC, TCA, TCG, AGT, AGC, AGA, GGA, TGA, CGA, ACT, and GCT, in which the universal codons and anitcodons correspond to at least 12 CTG codons in the wild-type DNA. Further, each internal primer overlaps with another internal or external primer in a manner that a mutant DNA encoding the *C. rugosa* lipase is obtained.

In a further aspect, this invention features a chimeric *C. rugosa* lipase including a substrate interacting domain of a first *C. rugosa* lipase and a non-substrate interacting domain (e.g., a carboxylesterase domain) of a second *C. rugosa* lipase. For example, the second *C. rugosa* lipase is a polypeptide of SEQ ID NO:6, and the first *C. rugosa* lipase is a polypeptide of SEQ ID NO:2, 4, 8, or 10.

Also within the scope of this invention is the use of afore-mentioned nucleic acid for the manufacture of a *C. rugosa* lipase for biocatalytic applications.

Other features, objects, and advantages of the invention will be apparent from the description and from the claims.

DETAILED DESCRIPTION

This invention relates to an isolated nucleic acid that includes a mutant DNA, which is at least 80% identical to a wild-type DNA encoding a *C. rugosa* lipase.

Set forth below are the mutant nucleic acid sequences of *C. rugosa* lipase 2, *C. rugosa* lipase 3, *C. rugosa* lipase 4, *C. rugosa* lipase 5, and *C. rugosa* lipase 8, wherein all the CTG codons corresponding to serine in the wild-type DNA have been substituted with one of the six universal serine codons (i.e., TCT, TCC, TCA, TCG, AGT, or AGC). The mutated nucleotides are represented in black background. Also shown are the encoded amino acid sequences. The introduced N-terminal peptide (i.e., SMNSRGPAGRLGS) is underlined. Mutated amino acid residues are rendered in bold.

Applicant : Jei-Fu Shaw et al.
Serial No. : 09/943,857
Filed : August 31, 2001
Page : 3 of 27

Attorney's Docket No.: 08919-066001 / 09A-900517

Mutant *C. rugosa* lipase 2

```
TCGATGAATTCACGTGGCCCAGCCGGCCGTCTCGGATCGGTACCCACCGCCACGCTCGCC  60
 S   M   N   S   R   G   P   A   G   R   L   G   S   V   P   T   A   T   L   A   20
```

| Applicant | : Jei-Fu Shaw et al. |
|---|---|
| Serial No. | : 09/943,857 |
| Filed | : August 31, 2001 |
| Page | : 4 of 27 |

Attorney's Docket No.: 08919-066001 / 09A-900517

```
AACGGCGACACCATCACCGGTCTCAACGCCATTGTCAACGAAAAGTTTCTCGGCATACCG  120
 N  G  D  T  I  T  G  L  N  A  I  V  N  E  K  F  L  G  I  P   40
TTTGCCGAGCCGCCCGTGGGCAGCCTCCGCTTCAAGCCGCCCGTGCCGTACTCGGCGTCG  180
 F  A  E  P  P  V  G  S  L  R  F  K  P  P  V  P  Y  S  A  S   60
CTCAACGGCCAGCAGTTTACCTCTTACGGCCCGTCTTGCATGCAGATGAACCCTATGGGC  240
 L  N  G  Q  Q  F  T  S  Y  G  P  S  C  M  Q  M  N  P  M  G   80
TCGTTTGAGGACACACTTCCCAAGAATGCGCTTGACTTGGTGCTCCAGTCCAAGATCTTC  300
 S  F  E  D  T  L  P  K  N  A  L  D  L  V  L  Q  S  K  I  F  100
CAAGTGGTGCTTCCCAACGACGAGGACTGTCTCACCATCAACGTGATCCGGCCGCCCGGC  360
 Q  V  V  L  P  N  D  E  D  C  L  T  I  N  V  I  R  P  P  G  120
ACCAGGGCCAGTGCTGGTCTCCCGGTGATGCTCTGGATCTTTGGCGGTGGGTTTGAGCTT  420
 T  R  A  S  A  G  L  P  V  M  L  W  I  F  G  G  G  F  E  L  140
GGCGGCTCCAGCCTCTTTCCAGGAGACCAGATGGTGGCCAAGAGCGTGCTCATGGGTAAA  480
 G  G  S  S  L  F  P  G  D  Q  M  V  A  K  S  V  L  M  G  K  160
CCGGTGATCCACGTGAGCATGAACTACCGCGTGGCGTCATGGGGGTTCTTGGCCGGCCCC  540
 P  V  I  H  V  S  M  N  Y  R  V  A  S  W  G  F  L  A  G  P  180
GACATCCAGAACGAAGGCAGCGGGAACGCCGGCTTGCATGACCAGCGCTTGGCCATGCAG  600
 D  I  Q  N  E  G  S  G  N  A  G  L  H  D  Q  R  L  A  M  Q  200
TGGGTGGCGGACAACATTGCTGGGTTTGGCGGCGACCCGAGCAAGGTGACCATATACGGC  660
 W  V  A  D  N  I  A  G  F  G  G  D  P  S  K  V  T  I  Y  G  220
GAGTCTGCGGGCAGCATGTCGACGTTTGTGCACCTTGTGTGGAACGACGGCGACAACACG  720
 E  S  A  G  S  M  S  T  F  V  H  L  V  W  N  D  G  D  N  T  240
TACAACGGCAAGCCGTTGTTCCGCGCCGCCATCATGCAGTCTGGCTGCATGGTGCCGTCT  780
 Y  N  G  K  P  L  F  R  A  A  I  M  Q  S  G  C  M  V  P  S  260
GACCCGGTGGACGGCACGTACGGCACCGAGATCTACAACCAGGTGGTGGCGTCTGCCGGG  840
 D  P  V  D  G  T  Y  G  T  E  I  Y  N  Q  V  V  A  S  A  G  280
```

Applicant : Jei-Fu Shaw et al.
Serial No. : 09/943,857
Filed : August 31, 2001
Page : 5 of 27

Attorney's Docket No.: 08919-066001 / 09A-900517

```
TGTGGCAGTGCCAGCGACAAGCTCGCGTGCTTGCGCGGCCTTTCTCAGGACACGTTGTAC 900
 C  G  S  A  S  D  K  L  A  C  L  R  G  L  S  Q  D  T  L  Y  300
CAGGCCACGAGCGACACGCCCGGCGTGTTGGCGTACCCGTCGTTGCGGTTGTCTTATCTC 960
 Q  A  T  S  D  T  P  G  V  L  A  Y  P  S  L  R  L  S  Y  L  320
CCGCGGCCCGACGGCACCTTCATCACCGACGACATGTATGCCTTGGTGCGGGACGGCAAG 1020
 P  R  P  D  G  T  F  I  T  D  D  M  Y  A  L  V  R  D  G  K  340
TACGCACACGTGCCGGTGATCATCGGCGACCAGAACGACGAGGGCACTTTGTTTGGGCTC 1080
 Y  A  H  V  P  V  I  I  G  D  Q  N  D  E  G  T  L  F  G  L  360
TCTTCTTTGAACGTGACCACAGATGCTCAGGCACGGGCGTACTTCAAGCAGTCTTTCATC 1140
 S  S  L  N  V  T  T  D  A  Q  A  R  A  Y  F  K  Q  S  F  I  380
CACGCCAGCGATGCGGAGATCGACACGTTGATGGCGGCGTACACCAGCGACATCACCCAG 1200
 H  A  S  D  A  E  I  D  T  L  M  A  A  Y  T  S  D  I  T  Q  400
GGTTCTCCGTTCGACACCGGCATCTTCAATGCCATCACCCCGCAGTTCAAACGGATCTCT 1260
 G  S  P  F  D  T  G  I  F  N  A  I  T  P  Q  F  K  R  I  S  420
GCGTTGCTTGGCGACCTTGCGTTCACGCTTGCGCGTCGCTACTTCCTCAACTACTACCAG 1320
 A  L  L  G  D  L  A  F  T  L  A  R  R  Y  F  L  N  Y  Y  Q  440
GGCGGCACCAAGTACTCGTTCCTCTCTAAGCAGCTTTCTGGGTTGCCCGTCTTGGGCACC 1380
 G  G  T  K  Y  S  F  L  S  K  Q  L  S  G  L  P  V  L  G  T  460
TTCCACGGCAACGACATCATCTGGCAGGACTACTTGGTGGGCAGCGGCAGTGTGATCTAC 1440
 F  H  G  N  D  I  I  W  Q  D  Y  L  V  G  S  G  S  V  I  Y  480
AACAACGCGTTCATTGCGTTTGCCAACGACCTCGACCCGAACAAGGCGGGCTTGTGGACC 1500
 N  N  A  F  I  A  F  A  N  D  L  D  P  N  K  A  G  L  W  T  500
AACTGGCCCACGTACACCAGCAGCTCTCAGTCTGGCAACAACTTGATGCAGATCAACGGC 1560
 N  W  P  T  Y  T  S  S  Q  S  G  N  N  L  M  Q  I  N  G  520
TTGGGGTTGTACACCGGCAAGGACAACTTCCGCCCGGATGCGTACAGCGCCCTCTTTTCC 1620
 L  G  L  Y  T  G  K  D  N  F  R  P  D  A  Y  S  A  L  F  S  540
```

| | |
|---|---|
| Applicant : Jei-Fu Shaw et al. | Attorney's Docket No.: 08919-066001 / 09A-900517 |
| Serial No. : 09/943,857 | |
| Filed : August 31, 2001 | |
| Page : 6 of 27 | |

```
AACCCGCCGTCTTTCTTTGTG  (SEQ ID NO:1)                           1641

N   P   P   S   F   F   V  (SEQ ID NO:2)                      547
```

Mutant *C. rugosa* lipase 3

```
TCGATGAATTCACGTGGCCCAGCCGGCCGTCTCGGATCGGTACCCACCGCCAAGCTCGCC   60
  S   M   N   S   R   G   P   A   G   R   L   G   S   V   P   T   A   K   L   A   20
AACGGCGACACCATCACCGGTCTCAACGCCATCATCAACGAGGCGTTCCTCGGCATTCCC  120
  N   G   D   T   I   T   G   L   N   A   I   I   N   E   A   F   L   G   I   P   40
TTTGCCGAGCCGCCGGTGGGCAACCTCCGCTTCAAGGACCCTGTGCCGTACTCTGGCTCG  180
  F   A   E   P   P   V   G   N   L   R   F   K   D   P   V   P   Y   S   G   S   60
CTCAACGGCCAGAAGTTCACTTCTTACGGCCCGTCTTGCATGCAGCAGAACCCCGAGGGC  240
  L   N   G   Q   K   F   T   S   Y   G   P   S   C   M   Q   Q   N   P   E   G   80
ACGTTTGAAGAGAACCTTGGCAAGACGGCACTCGACTTGGTGATGCAGTCCAAGGTGTTC  300
  T   F   E   E   N   L   G   K   T   A   L   D   L   V   M   Q   S   K   V   F  100
CAGGCGGTGCTTCCCCAGAGTGAGGACTGCCTCACCATCAACGTGGTGCGGCCGCCGGGC  360
  Q   A   V   L   P   Q   S   E   D   C   L   T   I   N   V   V   R   P   P   G  120
ACCAAGGCGGGCGCCAACCTCCCGGTCATGCTCTGGATCTTTGGCGGTGGGTTTGAGATC  420
  T   K   A   G   A   N   L   P   V   M   L   W   I   F   G   G   G   F   E   I  140
GGCAGCCCCACCATCTTCCCTCCCGCCCAGATGGTCACCAAGAGTGTGCTCATGGGCAAG  480
  G   S   P   T   I   F   P   P   A   Q   M   V   T   K   S   V   L   M   G   K  160
CACATCATCCACGTGGCCGTCAACTACCGTGTTGCCTCGTGGGGGTTCTTGGCTGGTGAT  540
  H   I   I   H   V   A   V   N   Y   R   V   A   S   W   G   F   L   A   G   D  180
GACATCAAGGCCGAGGGCAGCGGGAACGCCGGCTTGAAGGACCAGCGTTTGGGCATGCAG  600
  D   I   K   A   E   G   S   G   N   A   G   L   K   D   Q   R   L   G   M   Q  200
TGGGTGGCAGACAACATTGCCGGGTTCGGCGGCGACCCGAGCAAGGTGACTATCTTTGGC  660
```

Applicant : Jei-Fu Shaw et al.  
Serial No. : 09/943,857  
Filed : August 31, 2001  
Page : 7 of 27

Attorney's Docket No.: 08919-066001 / 09A-900517

```
        W   V   A   D   N   I   A   G   F   G   G   D   P   S   K   V   T   I   F   G   220
        GAGTCTGCGGGCAGCATGTCCGTGTTGTGCCACCTCATCTGGAACGACGGCGACAACACG   720
        E   S   A   G   S   M   S   V   L   C   H   L   I   W   N   D   G   D   N   T   240
        TACAAGGGCAAGCCGTTGTTCCGCGCGGGCATCATGCAGTCTGGAGCCATGGTGCCGTCT   780
        Y   K   G   K   P   L   F   R   A   G   I   M   Q   S   G   A   M   V   P   S   260
        GACCCGGTGGACGGCACGTACGGCAACGAGATCTACGACCTCTTTGTCTCGAGTGCTGGC   840
        D   P   V   D   G   T   Y   G   N   E   I   Y   D   L   F   V   S   S   A   G   280
        TGTGGCAGCGCCAGCGACAAGCTCGCGTGCTTGCGCAGTGCGTCTAGCGACACCTTGCTC   900
        C   G   S   A   S   D   K   L   A   C   L   R   S   A   S   S   D   T   L   L   300
        GATGCCACCAACAACACTCCTGGGTTCTTGGCGTACTCCTCGTTGCGGTTGTCTTATCTC   960
        D   A   T   N   N   T   P   G   F   L   A   Y   S   S   L   R   L   S   Y   L   320
        CCGCGGCCCGACGGCAAGAACATCACCGATGACATGTACAAGTTGGTGCGCGACGGCAAG   1020
        P   R   P   D   G   K   N   I   T   D   D   M   Y   K   L   V   R   D   G   K   340
        TATGCAAGCGTTCCCGTGATCATTGGCGACCAGAACGACGAGGGCACCATCTTTGGGCTC   1080
        Y   A   S   V   P   V   I   I   G   D   Q   N   D   E   G   T   I   F   G   L   360
        TCTTCTTTGAACGTGACCACGAATGCTCAGGCCCGTGCTTACTTCAAGCAGTCTTTCATC   1140
        S   S   L   N   V   T   T   N   A   Q   A   R   A   Y   F   K   Q   S   F   I   380
        CACGCCAGCGACGCGGAGATCGACACCTTGATGGCGGCGTACCCCCAGGACATCACCCAG   1200
        H   A   S   D   A   E   I   D   T   L   M   A   A   Y   P   Q   D   I   T   Q   400
        GGTTCTCCGTTCGACACGGGTGTTCTCAACGCCCCTCACCCCGCAGTTCAAGAGAATCTCT   1260
        G   S   P   F   D   T   G   V   L   N   A   L   T   P   Q   F   K   R   I   S   420
        GCGGTGCTCGGCGACCTTGCATTCATCCACGCCCGCCGCTACTTCCTCAACCACTTCCAG   1320
        A   V   L   G   D   L   A   F   I   H   A   R   R   Y   F   L   N   H   F   Q   440
        GGCGGCACCAAGTACTCGTTCCTCTCTAAGCAGCTCTCTGGGTTGCCAATCATGGGCACC   1380
        G   G   T   K   Y   S   F   L   S   K   Q   L   S   G   L   P   I   M   G   T   460
        TTCCATGCCAACGACATTGTGTGGCAGGACTACTTGTTGGGAAGCGGCAGCGTCATCTAC   1440
```

Applicant : Jei-Fu Shaw et al.  
Serial No. : 09/943,857  
Filed : August 31, 2001  
Page : 8 of 27

Attorney's Docket No.: 08919-066001 / 09A-900517

```
  F   H   A   N   D   I   V   W   Q   D   Y   L   L   G   S   G   S   V   I   Y    480
AACAACGCGTTTATCGCGTTCGCCACCGACTTGGACCCCAACACCGCGGGGTTGTTGGTG              1500
  N   N   A   F   I   A   F   A   T   D   L   D   P   N   T   A   G   L   L   V    500
AACTGGCCCAAGTACACCAGCAGCTCTCAGTCTGGCAACAACTTGATGATGATCAACGCC              1560
  N   W   P   K   Y   T   S   S   S   Q   S   G   N   N   L   M   M   I   N   A    520
TTGGGCTTGTACACCGGCAAGGACAACTTCCGCACCGCTGGCTACGACGCGTTGATGACC              1620
  L   G   L   Y   T   G   K   D   N   F   R   T   A   G   Y   D   A   L   M   T    540
AACCCGTCTTCTTTCTTTGTG  (SEQ ID NO:3)                                       1641
  N   P   S   S   F   F   V  (SEQ ID NO:4)                                  547
```

Mutant *C. rugosa* lipase 4

```
TCGATGAATTCACGTGGCCCAGCCGGCCGTCTCGGATCGGTACCCACTGCCACGCTCGCC               60
  S   M   N   S   R   G   P   A   G   R   L   G   S   V   P   T   A   T   L   A    20
AACGGCGACACCATCACCGGTCTCAACGCCATCATCAACGAGGCGTTCCTCGGTATTCCC              120
  N   G   D   T   I   T   G   L   N   A   I   I   N   E   A   F   L   G   I   P    40
TTTGCTCAGCCGCCGGTGGGCAACCTCCGCTTCAAGCCGCCTGTGCCGTACTCGGCGTCT              180
  F   A   Q   P   P   V   G   N   L   R   F   K   P   P   V   P   Y   S   A   S    60
CTCAATGGTCAGAAGTTTACTTCGTATGGCCCTTCGTGCATGCAGATGAACCCATTGGGC              240
  L   N   G   Q   K   F   T   S   Y   G   P   S   C   M   Q   M   N   P   L   G    80
AACTGGGACTCCTCGCTTCCCAAGGCTGCCATCAACTCCTTGATGCAGTCCAAGCTCTTC              300
  N   W   D   S   S   L   P   K   A   A   I   N   S   L   M   Q   S   K   L   F    100
CAGGCGGTGCTTCCTAACGGCGAGGACTGTCTCACCATCAACGTGGTGCGGCCGTCAGGC              360
  Q   A   V   L   P   N   G   E   D   C   L   T   I   N   V   V   R   P   S   G    120
ACCAAGCCGGGTGCCAACCTCCCCGTGATGGTGTGGATTTTTGGCGGCGGGTTTGAGGTT              420
  T   K   P   G   A   N   L   P   V   M   V   W   I   F   G   G   G   F   E   V    140
GGCGGCTCCAGTCTCTTCCCTCCCGCACAGATGATCACCGCCAGCGTGCTTATGGGCAAG              480
```

| | | | | | | | | | | | | | | | | |
|---|---|---|---|---|---|---|---|---|---|---|---|---|---|---|---|---|
|G|G|S|S|L|F|P|P|A|Q|M|I|T|A|S|V|L|M|G|K|160|

CCCATCATCCACGTGAGCATGAACTACCGCGTTGCTTCGTGGGGGTTCTTGGCTGGTCCA 540

P I I H V S M N Y R V A S W G F L A G P 180

GACATCAAGGCCGAGGGCAGCGGGAACGCCGGTTTGCACGACCAACGCTTGGGTTTGCAG 600

D I K A E G S G N A G L H D Q R L G L Q 200

TGGGTGGCGGACAACATTGCCGGGTTCGGCGGCGACCCGTCCAAGGTGACCATCTTTGGT 660

W V A D N I A G F G G D P S K V T I F G 220

GAGTCGGCGGGCAGCATGTCGGTAATGTGTCAGCTCCTCTGGAACGACGGCGACAACACG 720

E S A G S M S V M C Q L L W N D G D N T 240

TACAACGGCAAGCCGTTGTTCCGTGCCGCCATCATGCAGTCTGGGGCCATGGTGCCGTCG 780

Y N G K P L F R A A I M Q S G A M V P S 260

GACCCGGTGGATGGGCCCTACGGCACGCAGATCTACGACCAGGTGGTTGCTTCAGCCGGC 840

D P V D G P Y G T Q I Y D Q V V A S A G 280

TGTGGCAGTGCCAGCGACAAGCTCGCGTGCTTGCGCAGCATCTCGAACGACAAACTCTTC 900

C G S A S D K L A C L R S I S N D K L F 300

CAGGCCACCAGCGACACTCCGGGGGCCTTGGCGTACCCCTCGTTGCGGTTGTCGTTTCTC 960

Q A T S D T P G A L A Y P S L R L S F L 320

CCGCGGCCCGACGGCACCTTCATCACCGATGACATGTTCAAGTTGGTGCGCGACGGCAAG 1020

P R P D G T F I T D D M F K L V R D G K 340

TGTGCCAACGTTCCGGTGATCATTGGCGACCAGAACGACGAGGGCACAGTGTTTGCGTTG 1080

C A N V P V I I G D Q N D E G T V F A L 360

TCCAGCTTGAACGTGACTACGGATGCTCAGGCACGCCAGTACTTCAAGGAAAGCTTCATC 1140

S S L N V T T D A Q A R Q Y F K E S F I 380

CACGCCAGCGACGCGGAGATCGACACCTTGATGGCGGCGTACCCCAGCGACATCACCCAG 1200

H A S D A E I D T L M A A Y P S D I T Q 400

GGTAGTCCGTTCGACACCGGCATCTTCAACGCCATCACCCCGCAGTTCAAACGGATTGCA 1260

Applicant : Jei-Fu Shaw et al.
Serial No. : 09/943,857
Filed : August 31, 2001
Page : 10 of 27

Attorney's Docket No.: 08919-066001 / 09A-900517

```
                    G   S   P   F   D   T   G   I   F   N   A   I   T   P   Q   F   K   R   I   A   420
GCGGTGCTTGGTGACCTTGCGTTCACTCTCCCCCGGCGCTACTTCCTCAACCACTTCCAG                                           1320
                    A   V   L   G   D   L   A   F   T   L   P   R   R   Y   F   L   N   H   F   Q   440
GGCGGCACCAAGTACTCGTTCCTCTCGAAGCAGCTTAGTGGGTTGCCGGTGATTGGCACC                                           1380
                    G   G   T   K   Y   S   F   L   S   K   Q   L   S   G   L   P   V   I   G   T   460
CACCACGCCAACGACATTGTGTGGCAGGACTTTTTGGTGAGCCACAGCAGCGCCGTGTAC                                           1440
                    H   H   A   N   D   I   V   W   Q   D   F   L   V   S   H   S   S   A   V   Y   480
AACAACGCGTTTATTGCCTTTGCCAACGACCTCGACCCGAACAAGGCCGGTTTGCTTGTG                                           1500
                    N   N   A   F   I   A   F   A   N   D   L   D   P   N   K   A   G   L   L   V   500
AACTGGCCCAAGTACACCAGCAGCTCTCAGTCAGGCAACAACTTGTTGCAGATCAACGCC                                           1560
                    N   W   P   K   Y   T   S   S   S   Q   S   G   N   N   L   L   Q   I   N   A   520
TTGGGCTTGTACACCGGCAAGGACAACTTCCGCACCGCTGGCTACGACGCGTTGTTTACC                                           1620
                    L   G   L   Y   T   G   K   D   N   F   R   T   A   G   Y   D   A   L   F   T   540
AACCCGTCTTCTTTCTTTGTG  (SEQ ID NO:5)                                                                   1641
                    N   P   S   F   F   V   (SEQ ID NO:6)                                              547
```

Mutant *C. rugosa* lipase 5

```
TCGATGAATTCACGTGGCCCAGCCGGCCGTCTCGGATCGGTACCCACTGCCACGCTCGCC          60
  S   M   N   S   R   G   P   A   G   R   L   G   S   V   P   T   A   T   L   A      20
AACGGCGACACCATCACCGGTCTCAACGCCATCATCAACGAGGCGTTCCTCGGCATTCCC         120
  N   G   D   T   I   T   G   L   N   A   I   I   N   E   A   F   L   G   I   P      40
TTTGCCGAGCCGCCGGTGGGCAACCTCCGCTTCAAGGACCCTGTGCCGTACCGTGGGTCT         180
  F   A   E   P   P   V   G   N   L   R   F   K   D   P   V   P   Y   R   G   S      60
CTCAACGGTCAATCCTTCACCGCGTACGGTCCGTCTTGCATGCAGCAGAACCCCGAGGGC         240
  L   N   G   Q   S   F   T   A   Y   G   P   S   C   M   Q   Q   N   P   E   G      80
ACCTACGAGGAGAACCTCCCCAAGGTGGCGCTTGACTTGGTGATGCAGTCCAAGGTGTTC         300
```

| | | | | | | | | | | | | | | | | |
|---|---|---|---|---|---|---|---|---|---|---|---|---|---|---|---|---|
| T | Y | E | E | N | L | P | K | V | A | L | D | L | V | M | Q | S | K | V | F | 100 |

CAGGCTGTTCTCCCCAACAGCGAGGACTGCCTCACCATCAACGTGGTGCGGCCGCCGGGC 360

Q A V L P N S E D C L T I N V V R P P G 120

ACCAAGGCGGGCGCCAACCTCCCGGTCATGCTCTGGATCTTTGGCGGTGGGTTTGAGATC 420

T K A G A N L P V M L W I F G G G F E I 140

GGCAGCCCCACCATCTTCCCTCCCGCTCAGATGGTCTCCAAGAGTGTGCTCATGGGCGAG 480

G S P T I F P P A Q M V S K S V L M G E 160

CCCATCATCCACGTGGCCGTCAACTACCGCTTGGCGTCCTTTGGTTTCTTGGCCGGTCCG 540

P I I H V A V N Y R L A S F G F L A G P 180

GACATCAAGGCCGAGGGCAGCTCCAATGCCGGCCTCAAGGACCAGCGCTTGGGCATGCAG 600

D I K A E G S S N A G L K D Q R L G M Q 200

TGGGTGGCAGACAACATTGCCGGGTTCGGCGGCGACCCGAGCAAGGTGACCATCTTTGGC 660

W V A D N I A G F G G D P S K V T I F G 220

GAGTCTGCGGGCAGCATGTCCGTGTTGTGCCACCTTCTCTGGAATGGCGGCGACAACACG 720

E S A G S M S V L C H L L W N G G D N T 240

TACAAGGGCAAGCCGTTGTTCCGCGCGGGCATCATGCAGTCTGGAGCCATGGTGCCGTCT 780

Y K G K P L F R A G I M Q S G A M V P S 260

GACCCGGTGGACGGCACCTATGGAGCCCAAATCTATGACACGTTGGTGGCTTCTACGGGC 840

D P V D G T Y G A Q I Y D T L V A S T G 280

TGCAGCAGTGCCAGCAACAAGCTTGCGTGCTTGCGTGGTCTTTCTACTCAGGCATTGCTC 900

C S S A S N K L A C L R G L S T Q A L L 300

GATGCCACCAACGACACCCCTGGGTTCTTGTCGTACACCTCGTTGCGGTTGTCTTATCTC 960

D A T N D T P G F L S Y T S L R L S Y L 320

CCGCGGCCCGACGGCGCCAACATCACCGATGACATGTACAAGTTGGTACGCGACGGCAAG 1020

P R P D G A N I T D D M Y K L V R D G K 340

TATGCAAGCGTTCCCGTGATCATTGGCGACCAGAACGACGAGGGCTTCTTGTTTGATCTC 1080

| | | | | | | | | | | | | | | | | |
|---|---|---|---|---|---|---|---|---|---|---|---|---|---|---|---|---|
| Y | A | S | V | P | V | I | I | G | D | Q | N | D | E | G | F | L | F | D | L | 360 |

TCTTCTTTGAACACCACCACCGAGGCCGACGCCGAGGCATACCTCAGAAAGTCTTTCATC 1140

| S | S | L | N | T | T | E | A | D | A | E | A | Y | L | R | K | S | F | I | 380 |

CACGCCACCGACGCCGATATCACCGCATTGAAGGCGGCGTACCCCAGCGATGTCACCCAG 1200

| H | A | T | D | A | D | I | T | A | L | K | A | A | Y | P | S | D | V | T | Q | 400 |

GGTTCTCCGTTCGACACGGGCATTCTCAACGCCCTTACACCCCAGCTCAAGCGGATCAAT 1260

| G | S | P | F | D | T | G | I | L | N | A | L | T | P | Q | L | K | R | I | N | 420 |

GCTGTGCTTGGCGACCTCACCTTTACCCTCTCGCGCCGCTACTTCCTCAACCACTACACC 1320

| A | V | L | G | D | L | T | F | T | L | S | R | R | Y | F | L | N | H | Y | T | 440 |

GGTGGTCCCAAGTACTCGTTCCTCTCTAAGCAGCTTTCTGGGTTGCCCATTCTCGGTACG 1380

| G | G | P | K | Y | S | F | L | S | K | Q | L | S | G | L | P | I | L | G | T | 460 |

TTCCACGCGAACGACATTGTGTGGCAGCACTTTTTGTTGGGCAGCGGCAGCGTCATCTAC 1440

| F | H | A | N | D | I | V | W | Q | H | F | L | L | G | S | G | S | V | I | Y | 480 |

AACAACGCGTTCATCGCGTTTGCCACCGACTTGGACCCCAACACCGCGGGCTTGTCTGTG 1500

| N | N | A | F | I | A | F | A | T | D | L | D | P | N | T | A | G | L | S | V | 500 |

CAGTGGCCCAAGTACACCAGCAGCTCTCAGGCGGGGGACAACTTGATGCAGATCAGTGCC 1560

| Q | W | P | K | Y | T | S | S | S | Q | A | G | D | N | L | M | Q | I | S | A | 520 |

TTGGGCTTGTACACCGGCAAGGACAACTTCCGCACCGCCGGCTACAACGCTTTGTTTGCC 1620

| L | G | L | Y | T | G | K | D | N | F | R | T | A | G | Y | N | A | L | F | A | 540 |

GACCCGTCTCACTTTTTCGTG (SEQ ID NO:7)  1641

| D | P | S | H | F | F | V | (SEQ ID NO:8) | 547 |

Mutant *C. rugosa* lipase 8

TCGATGAATTCACGTGGCCCAGCCGGCCGTCTCGGATCGGTACCCACTGCCACGCTCGCC 60

| S | M | N | S | R | G | P | A | G | R | L | G | S | V | P | T | A | T | L | A | 20 |

AACGGCGACACCATCACCGGTCTCAACGCCATCATCAACGAGGCGTTCCTCGGCATTCCC 120

| N | G | D | T | I | T | G | L | N | A | I | I | N | E | A | F | L | G | I | P | 40 |

Applicant : Jei-Fu Shaw et al.
Serial No. : 09/943,857
Filed : August 31, 2001
Page : 13 of 27

```
TTTGCCGAGCCGCCGGTGGGCAACCTCCGCTTCAAGGACCCCGTGCCGTACTCCGGCTCG  180
 F   A   E   P   P   V   G   N   L   R   F   K   D   P   V   P   Y   S   G   S    60
CTCGATGGCCAGAAGTTCACTTCTTACGGCCCGTCTTGCATGCAGCAGAACCCCGAGGGC  240
 L   D   G   Q   K   F   T   S   Y   G   P   S   C   M   Q   Q   N   P   E   G    80
ACCTACGAGGAGAACCTCCCCAAGGCAGCGCTCGACTTGGTGATGCAGTCCAAGGTGTTT  300
 T   Y   E   E   N   L   P   K   A   A   L   D   L   V   M   Q   S   K   V   F   100
GAGGCGGTGTCTCCGTCTAGCGAGGACTGTCTCACCATCAACGTGGTGCGGCCGCCGGGC  360
 E   A   V   S   P   S   S   E   D   C   L   T   I   N   V   V   R   P   P   G   120
ACCAAGGCGGGTGCCAACCTCCCGGTGATGCTCTGGATCTTTGGCGGCGGGTTTGAGGTG  420
 T   K   A   G   A   N   L   P   V   M   L   W   I   F   G   G   G   F   E   V   140
GGTGGCACCAGCACCTTCCCTCCCGCCCAGATGATCACCAAGAGCATTGCCATGGGCAAG  480
 G   G   T   S   T   F   P   P   A   Q   M   I   T   K   S   I   A   M   G   K   160
CCCATCATCCACGTGAGCGTCAACTACCGCGTGTCGTCGTGGGGGTTCTTGGCTGGCGAC  540
 P   I   I   H   V   S   V   N   Y   R   V   S   S   W   G   F   L   A   G   D   180
GAGATCAAGGCCGAGGGCAGTGCCAACGCCGGTTTGAAGGACCAGCGCATGGGCATGCAG  600
 E   I   K   A   E   G   S   A   N   A   G   L   K   D   Q   R   M   G   M   Q   200
TGGGTGGCGGACAACATTGCGGCGTTTGGCGGCGACCCGACCAAGGTGACCATCTTTGGC  660
 W   V   A   D   N   I   A   A   F   G   G   D   P   T   K   V   T   I   F   G   220
GAGTCTGCGGGCAGCATGTCGGTCATGTGCCACATTCTCTGGAACGACGGCGACAACACG  720
 E   S   A   G   S   M   S   V   M   C   H   I   L   W   N   D   G   D   N   T   240
TACAAGGGCAAGCCGCTCTTCCGCGCGGGCATCATGCAGTCTGGGGCCATGGTACCGTCG  780
 Y   K   G   K   P   L   F   R   A   G   I   M   Q   S   G   A   M   V   P   S   260
GACGCGGTGGACGGCGTCTACGGCAACGAGATCTTTGACCTCTTGGCGTCGGACGCGGGC  840
 D   A   V   D   G   V   Y   G   N   E   I   F   D   L   L   A   S   D   A   G   280
TGCGGCAGCGCCAGCGACAAGCTTGCGTGCTTGCGCGGTGTGTCTAGCGACACGTTGGAG  900
 C   G   S   A   S   D   K   L   A   C   L   R   G   V   S   S   D   T   L   E   300
```

```
GACGCCACCAACAACACCCCTGGGTTCTTGGCGTACTCCTCGTTGCGGTTGTCTTATCTC  960
 D   A   T   N.  N   T   P   G   F   L   A   Y   S   S   L   R   L   S   Y   L   320
CCGCGGCCCGACGGCGTGAACATCACCGACGACATGTTTGCCTTGGTCCGCGAGGGCAAG 1020
 P   R   P   D   G   V   N   I   T   D   D   M   F   A   L   V   R   E   G   K   340
TATGCAAGCGTTCCTGTGATCATCGGCGACCAGAACGACGAGGGCACCTTCTTTGGCACC 1080
 Y   A   S   V   P   V   I   I   G   D   Q   N   D   E   G   T   F   F   G   T   360
TCTTCTTTGAACGTGACCACGGATGCCGAGGCCCGCCAGTACTTCACGCAGTCTTTTGTC 1140
 S   S   L   N   V   T   T   D   A   E   A   R   Q   Y   F   T   Q   S   F   V   380
CACGCCAGCGACGCGGAGCTCGACACGTTGATGACGGCGTACCCCCAGGACATCACCCAG 1200
 H   A   S   D   A   E   L   D   T   L   M   T   A   Y   P   Q   D   I   T   Q   400
GGTTCTCCGTTCGACACGGGTGTTCTCAACGCCCTCACCCCGCAGTTCAAGAGAATCTCT 1260
 G   S   P   F   D   T   G   V   L   N   A   L   T   P   Q   F   K   R   I   S   420
GCGGTGCTCGGCGACCTTGCCTTCATCCACGCCCGTCGCTACTTCCTCAACCACTACACC 1320
 A   V   L   G   D   L   A   F   I   H   A   R   R   Y   F   L   N   H   Y   T   440
GGCGGCACCAAGTACTCATTCCTCTCTAAGCAGCTCTCTGGCTTGCCGGTGCTCGGAACG 1380
 G   G   T   K   Y   S   F   L   S   K   Q   L   S   G   L   P   V   L   G   T   460
TTCCACTCCAACGACATTGTCTTCCAGGACTACTTGTTGGGCAGCGGCTCGCTCATCTAC 1440
 F   H   S   N   D   I   V   F   Q   D   Y   L   L   G   S   G   S   L   I   Y   480
AACAACGCGTTCATTGCGTTTGCCACGGACTTGGACCCCAACACCGCGGGGTTGTTGGTG 1500
 N   N   A   F   I   A   F   A   T   D   L   D   P   N   T   A   G   L   L   V   500
AAGTGGCCCGAGTACACCAGCAGCTCTCAGTCTGGCAACAACTTGATGATGATCAACGCC 1560
 K   W   P   E   Y   T   S   S   S   Q   S   G   N   N   L   M   M   I   N   A   520
TTGGGCTTGTACACCGGCAAGGACAACTCCCGCACCGCCGGCTACGACGCGTTGTTCTCC 1620
 L   G   L   Y   T   G   K   D   N   S   R   T   A   G   Y   D   A   L   F   S   540
AACCCGCCGTCTTTCTTTGTG  (SEQ ID NO:9)                          1641
 N   P   P   S   F   F   V   (SEQ ID NO:10)                    547 --
```

The differences between each mutant DNA and its corresponding wild-type DNA are due to replacement of the CTG codons with the universal serine codons, and in addition, can be due to degeneracy of genetic codons, which results in a DNA variant encoding, based on universal codons, a wild type *C. rugosa* lipase or a functionally equivalent amino acid sequence thereof. An isolated nucleic acid containing such a mutant DNA can be used to clone and express the *C. rugosa* lipase in a common host cell. A DNA variant can possess the codons preferred by a particular prokaryotic or eukaryotic host. The codons may be selected to increase the rate at which expression of a polypeptide occurs in the prokaryotic or eukaryotic host in accordance with the frequency with which the codons are utilized by the host. The mutant DNA can further include such variations as nucleotide substitutions, deletions, inversions, or insertions on the wild-type DNA. The variations can modify the cloning, processing, and expression of the *C. rugosa* lipase.

The just-described mutant DNA can be prepared based on site-directed mutagenesis, introducing very specific nucleotide substitutions (i.e., mutations) at defined locations in a nucleic acid sequence. See, for example, Zoller and Smith (1983) *Meth. Enzymol.* 100: 468; and *Molecular Cloning, A Laboratory Manual* (1989) Sambrook, Fritsch and Maniatis, Cold Spring Harbor, N.Y., chapter 15. Alternatively, the mutant DNA may be synthesized, in whole or in part, using chemical methods well known in the art. See Caruthers et al. (1980) *Nucl. Acids Res. Symp. Ser.* 215–223, and Horn et al. (1980) *Nucl Acids Res. Symp. Ser.* 225–232. In particular, introducing multiple mutations can be accomplished through various methods based on, e.g., polymerase chain reaction (PCR), ligase chain reaction (LCR), or overlap extension polymerase chain reaction. See Ge and Rudolph (1997) *BioTechniques* 22: 28–30.

The mutant DNA can encode a polypeptide of SEQ ID NO:2, 4, 6, 8, or 10. Alternatively, it can encode a polypeptide variant having an amino acid sequence that is 90% identical to, or differs by 1, 5, 10, 50, or more amino acid residues from, SEQ ID NO:2, 4, 6, 8, or 10. If alignment is needed for this comparison, the sequences should be aligned for maximum homology. The polypeptide variant is correlated with at least one catalytic activity of a polypeptide encoded by SEQ ID NO:2, 4, 6, 8, or 10, e.g., ester bond hydrolysis or esterification. A polypeptide variant may have "conservative" changes, wherein a substituted amino acid has similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). In some embodiments, a polypeptide variant may have "non-conservative" changes, e.g., replacement of a leucine with a methionine. Further, a polypeptide variant may also include amino acid deletions or insertions, or both. Guidance in determining which amino acid residues may be substituted, inserted, or deleted without abolishing the catalytic activity may be found using computer programs well known in the art, for example, DNASTAR software.

It is well known that cutinase is the smallest lipolytic enzyme with determined three-dimensional structure, and may be considered an esterase with a broader activity that also includes lipids. Based on the alignment of secondary structure (e.g., α-helix or β-strand), topology of the *C. rugosa* lipase polypeptide chain is similar to that of cutinase (the three dimensional structures of LIP1 and LIP3 have been determined. See, for example, Grochulski et al. (1993) *J Biol. Chem.* 268: 12843–12847; and Ghosh et al. (1995) *Structure* 3: 279–288). Therefore, according to the common folding pattern of lipase (Cygler et al. (1997) *Methods in Enzymol* 284: 3–37), the minimal functional fragment of *C. rugosa* lipase within the range of residues 100–456 can be determined (e.g., the β2 strand to α8, 9helix, totally about 350 amino acids and 1070 nucleotides).

The polypeptide having the amino acid sequence of SEQ ID NO:2 differs from the wild-type *C rugosa* lipase 2 a N-terminal peptide (i.e., SMNSRGPAGRLGS), and 4 amino acids (i.e., A14V; T48S; R91L; H92D). The polypeptide having the amino acid sequence of SEQ ID NO:4 differs form the wild-type *C. rugosa* lipase 3 by the N-terminal peptide and 5 amino acids (i.e., A14V; P161H; I408V; F409L; I412L). The polypeptide having the amino acid sequence of SEQ ID NO:6 differs form the wild-type *C. rugosa* lipase 4 by the N-terminal peptide and 1 amino acid (i.e., A14V). The polypeptide having the amino acid sequence of SEQ ID NO:8 differs from the wild-type *C. rugosa* lipase 5 by the N-terminal and 5 amino acids (i.e., A14V; K160E; T269A; G359D; S505Y). The polypeptide having the amino acid sequence of SEQ ID NO:10 differs from the wild-type *C. rugosa* lipase 1 by the N-terminal peptide and 17 amino acids (i.e., A14V; L197M; I266V; N278D; Y333F; N343S; I344V; Q370E; E373Q; K376T; I387L; G396Q; I408V; G427A; T429I; L430H; F530S).

The just-described polypeptide can be produced by using an expression vector that contains an isolated nucleic acid of this invention. As used herein, the term "vector" refers to a nucleic acid molecule capable of transporting another nucleic acid to which it has been linked and can include a plasmid, cosmid, or viral vector. A vector is capable of autonomous replication, and contains the nucleic acid of this invention in a form suitable for expression of the nucleic acid in a host cell. It includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory or inducible sequences. A vector can be designed for expression of a *C. rugosa* lipase in prokaryotic or eukaryotic cells, e.g., bacterial cells (e.g., *E. coli*), insect cells (e.g., using baculovirus expression vectors), yeast cells (e.g., *P. pastoris*), or mammalian cells. Suitable host cells are discussed further in Goeddel, (1990) *Gene Expression Technology: Methods in Enzymology* 185, Academic Press, San Diego, Calif. Expression of a *C. rugosa* lipase can be carried out with vectors containing constitutive or inducible promoters directing the expression of either fusion or non-fusion lipases. The fusion lipase may facilitate purification of soluble polypeptides. Fusion vectors add a number of amino acids to a polypeptide encoded therein, usually to the amino terminus of the polypeptide. Typical fusion expression vectors include pGEX (Pharmacia Biotech Inc; Smith and Johnson (1988) *Gene* 67:31–40), pMAL (New England Biolabs, Beverly, Mass.), and pRIT5 (Pharmacia, Piscataway, N.J.) which fuse glutathione S-transferase (GST), maltose E binding protein, or protein A, respectively, to the target polypeptide.

A vector can be introduced into host cells via conventional transformation or transfection techniques. As used herein, the terms "transformation" and "transfection" refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. A host cell of the invention can be used to express a C. rugosa lipase. The expressed C. rugosa lipase can be isolated from the host cell or a culture medium.

The present invention also provides a chimeric C. rugosa lipase that contains a substrate interacting domain of an isozyme and a non-substrate interacting domain of another isozyme. The "substrate interacting domain" refers to a fragment that is characterized by an approximated 32 amino acid sequence (e.g., amino acids of 63–94 of SEQ ID NO:8), and participates in substrate interactions. The "non-substrate interacting domains" include at least one catalytic domain, such as a carboxylesterase domain. The substrate interacting domain can be a part of the substrate binding region, which is generally dispersed along the full length amino acid sequence, and forms a tunnel to interact with, e.g., fatty acyl chain. See Cygler et al. (1999) *Biochim. Biophys. Acta* 1441: 205–214.

The carboxylesterase domain can catalyze hydrolysis of carboxylic esters, and include a catalytic triad: a serine, a glutamate (or aspartate), and a histidine. The sequence around the active site serine is well conserved and can be used as a signature pattern. See, e.g., Krejci et al. (1991) *Proc. Natl. Acad. Sci. USA* 88: 6647–6651(1991), or Cygler et al. (1993) *Protein Sci.* 2: 366–382. The chimeric polypeptide of this invention can be prepared by a domain shuffling method. For example, the method includes exchanging the SphI(184)-BstXI(304) restriction DNA fragments to obtain a recombinant nucleic acid encoding a mature chimeric C. rugosa lipase. The mature lipase contains a substrate interacting domain of an isozyme and non-substrate interacting sequences of another isozyme (e.g., LIP4). The recombinant nucleic acid is then ligated into a vector, e.g., pET-23a(+) *E. Coi.* T7 expression vector (Novagen) between Nde I and EcoRI sites.

Each of the just-described domains has at least 70% (e.g., 80%, 90%, 95%, or 100%) homology with its corresponding wild-type sequence, as long as its intended function in the chimeric polypeptide is retained. The chimeric polypeptide can be produced as a fusion chimeric polypeptide, e.g., a thioredoxin fused to the N-terminal of a chimeric polypeptide.

The specific example below is to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Expression of C. rugosa Lipase 2 (LIP2)

Materials and Methods

Strains and plasmids Plasmid-containing transformants were mainly grown in Luria-Bertani (LB) broth supplemented with ampicillin (100 µg/mL). The *P. pastoris* expression vector pGAPZα C (Invitrogen, Carlsbad, Calif.) was manipulated in *E. coli* strain TOP 10' grown in low salt Luria-Bertani (LB) broth (1% tryptone, 0.5% yeast extract, and 0.5% NaCl, pH 7.5) supplemented with zeocin (25 µg/mL). *P. pastoris* X-33 (wild type) was used for the expression of LIP2, and its transformants were cultured with YPD (0.1% yeast extract, 0.2% peptone, and 0.2% dextrose; pH 7.2) containing 100 µg/mL zeocin at 26° C.

Construction of expression vector. LIP2 has been sequenced previously (EMBL Databank accession number X64704). A PCR product containing the entire LIP2 coding region with a Kpn I restriction site at the 5' end and Not I site at the 3' end was prepared and cloned into the Kpn I-Not I sites of the *P. pastoris* expression vector pGAPZα C to generate pGAPZα-LIP2.

Transformation of plasmid DNAs into *P. pastoris*. Plasmid DNA (10 µg) harboring the engineered lipase gene was digested with EcoRV in a total volume of 20 µL for 2 h. Linearized plasmid was transformed into *P. pastoris* by the electroporation method. High voltage pulses (1.5 kV) were delivered to 100 µL samples in 0.2 cm electrode gap cuvettes (Bio-Rad Laboratories) by using a Gene Pulser electrophoration apparatus with the Pulse Controller (Bio-Rad Laboratories). Individual colonies of transformants were pitched and patched on tributyrin-emulsion YPD plates. The lipase-secreting transformants were identified by the clear zone on the opaque tributyrin emulsion. *P. pastoris* transformed with pGAPZαC was used as a negative control.

Purification of recombinant LIP2. The culture medium from *P. pastoris* was concentrated by ultrafiltration on a 30,000 molecular weight cut-off membrane. These samples were then applied onto a HIPREP 16/10 Octyl FF chromatographic column (Pharmacia Biotech). The column was washed with 5 column volumes of TE buffer plus 1 mM CHAPS and then 4 mM CHAPS. Bound proteins were then eluted with 5 column volumes of TE buffer containing 30 mM CHAPS. The eluted materials were dialyzed against TE buffer.

The eluted proteins were then applied to a HIPREP 16/10 Q XL column (Pharmacia Biotech) equilibrated with TE buffer and the proteins were eluted using a linear gradient of 0 to 300 mM $(NH_4)_2SO_4$ over 5 column volumes. Protein concentrations in the fractions were measured with the Bio-Rad assay kit and esterase activity was determined using p-nitrophenyl butyrate as a substrate. Purified proteins were stored in a storage buffer (60 mM KCl, 10 mM Tris-HCl, 1.25 mM EDTA, 1% Triton X-100, and 17% glycerol, pH 7.5) at −20° C.

Enzyme characterization. The molecular masses of the purified recombinant LIP2 and a commercial lipase (Lipase Type VII, Sigma) were determined by SDS-PAGE analysis. To analyze the thermal stability of lipase, samples were incubated at various temperatures from 37 to 100° C. for 10 minutes, and the residual activities were determined by spectrophotometric method (Redondo et al. (1995) *Biochim. Biophys. Acta* 1243 :15–24), using p-nitrophenyl caprylrate as a substrate at 37° C. The optimal reaction temperature for lipase was investigated at different temperatures from 10 to 60° C., and the activity was measured by spectrophotometric method using p-nitrophenyl butyrate as a substrate at pH 7.0. The optimal reaction pH for lipase was investigated at different pH from 3.0 to 9.0, and the activity was measured by spectrophotometric method using p-nitrophenyl butyrate as a substrate at 37° C.

The lipase activities were measured by titrimetry using triglycerides with various chain-length fatty acids as substrates. See Wang et al. (1988) *Biotechnol. Bioeng.* 31: 628–633. The release of free fatty acid was continuously monitored by titration with 1 mM NaOH on the pH-Stat. The esterase activity at 37° C. was determined spectrophotometrically using p-nitrophenyl esters as substrates. One unit of activity was defined as the smallest amount of enzyme able to release 1 µmol of p-nitrophenol per minute.

Results

Construction of Expression Plasmids and Overexpression of Recombinant LIP2 All 17 CTG codons of LIP2 gene were replaced with universal Ser codons (TCT) by simultaneous multiple site-directed mutagenesis. See Ge and Rudolph (1997) *BioTechniques.* 22: 28–30. The plasmid harboring the engineered LIP2 was transformed into *P. pastoris* by electroporation. The transformant cells were grown in 500-mL flasks containing 200 mL YPD medium for three days. The constitutive strong promoter of glyceraldehydes 3-phosphate dehydrogenase (GAP) allows the high level expression of LIP2. The majority of expressed LIP2 was secreted into the culture medium and the estimated amount of LIP2 was 2.3 mg/L. The transformants are highly stable and the produced LIP2 would be greatly increased in high cell density fermentation. See Cereghino and Cregg (2000) *FEMS Microbiol. Rev.* 24: 45–66.

Biochemical characterization of recombinant LIP2 The optimal pH of LIP2 was 7 and the enzyme showed 90% of activity at pH 6. In contrast, the optimal pHs of LIP4 and a commercial *C. rugosa* lipase (CRL) were pH 7–8 and 8, respectively. LIP2 showed much higher specific activity than LIP4 and CRL with p-nitrophenyl butyrate at all pH tested, especially at pH 6. The ratio of specific activity of LIP2, LIP4 and CRL was 100:4:3 at pH 6, whereas it was 100:80:25 at pH 8. Therefore, the LIP2 is especially useful at slightly acidic to neutral pH for industrial applications.

Further, the optimal temperatures for LIP2, LIP4 and CRL were 40–50, 40 and 37° C., respectively. The LIP2 showed broad optimum temperature range 30–50° C. and much higher specific activity than LIP4 and CRL at all temperature tested (10–60° C.). Unexpectedly, LIP2 showed quite high activity at low temperature, e.g., the specific activity at 10° C. was 1000 U/mg, which was 50% of that at optimum temperature. This suggested that the enzyme could be applied to the synthesis of labile compounds and low boiling point compounds at low temperature.

The enzyme activities after heating at various temperatures for 10 min were also compared. The LIP2 was more stable than either LIP4 or CRL at 50–70° C. After 10 min heating at 70° C., the residual activities for LIP2, LIP4 and CRL were 80%, 50% and 35%, respectively.

For the hydrolysis of p-nitrophenyl esters of various chain-length fatty acids (Table 1), LIP2, LIP4 and CRL showed different preference to ester substrates. The best substrates for LIP2, LIP4 and CRL were p-nitrophenyl palmitate, p-nitrophenyl palmitate and p-nitrophenyl caprylate, respectively. Both LIP2 and LIP4 showed much higher activity toward medium to long chain fatty acid esters ($C_{12}$–$C_{18}$), but LIP2 had 2–3 times higher activity than LIP4. For most the p-nitrophenyl esters including p-nitrophenyl butyrate, -caprylate, -caprate, -laurate, -myristate, -palmitate and -stearate, the specific activities were in the order: LIP2>LIP4>CRL.

Hydrolysis activities of triglycerides One important industrial application of lipases is the hydrolysis of fat and vegetable oils, which occur naturally as triglycerides, to produce fatty acids. See, e.g., Shaw et al. (1990) *Biotechnol. Bioeng.* 35: 132–137. Table 2 showed LIP2, LIP4 and CRL had different preference to triglyceride substrates. The best triglyceride substrates for LIP2, LIP4 and CRL were tributyrin, tricaprylin and tricaprylin, respectively.

For tributyrin, trilaurin, tripalmitin, tristearin and triolein, the specific activity of hydrolysis was in the following order: LIP2>LIP4>CRL. For triacetin and tricaproin, the order was LIP2>CRL>LIP4. For tricaprylin, the order was: LIP4>CRL>LIP2. For tricaprin and trimyristin, the order was: CRL>LIP2>LIP4. Therefore, different LIP isoforms should be used for different industrial applications in triglyceride hydrolysis.

Cholesterol esterase activity As shown in Table 3, LIP2 showed much higher specific activity of cholesterol esterase than LIP4 and CRL among three cholesteryl esters tested. Among various cholesteryl esters, cholesteryl laurate was the best substrate hydrolyzed by LIP2. Therefore, the LIP2 can be used as a useful cholesterol esterase for the applications in clinical chemistry, biochemistry and food analysis. Since about 70–80% of serum cholesterol is esterified with various chain-length and saturated fatty acids (Röschlau et al. (1974) 12: 403–407), therefore LIP2, which has cholesterol esterase activity, can be used for coupling with cholesterol oxidase and peroxidase to determine the serum cholesterol enzymatically. The high specific activity of LIP2 toward the various cholesteryl esters allows very efficient and accurate determination of the cholesterol esters in serum and food.

Synthesis of esters Lipase can efficiently catalyze the synthesis of various esters for industrial applications such as fruit-flavored products (e.g. beverages, candies, jellies, and jams), baked goods, wines, dairy products (e.g. cultured butter, sour cream, yogurt, and cheese), emulsifiers, lubricants and cosmetics. See, for example, Kim et al. (1998) *J. Am. Oil Chem. Soc.* 75: 1109–1113; Shaw and Lo (1994) *J. Am. Oil Chem. Soc.* 71: 715–719; or Shaw et al. (1991) *Enzyme Microb. Technol.* 13: 544–546. Table 4 showed that LIP2 was much better than either LIP4 or CRL in the synthesis of hexadecyl of octadecyl myristate, suggesting it favored long-chain alcohols in the esterification of myristic acid with equimolar mixtures of different alcohols. In contrast, CRL was the best for the synthesis of hexyl-, octyl- and dodecyl-myristate, suggesting it favored medium to short chain alcohols for myristic ester synthesis.

Table 5 showed that LIP2 had much higher activity for the synthesis of propyl butyrate than either LIP4 or CRL, suggesting it favored short chain acids in the esterification of n-propanol with equimolar mixtures of different chain length fatty acids. In contrast, LIP4 was the best for the synthesis of propyl dodecanoate, hexadecanoate and octadecanoate, suggesting it favored medium to long chain fatty acids for propyl ester synthesis.

TABLE 1

Hydrolysis of p-nitrophenyl (p-NP) esters of various chain-length fatty acids.

| | (U/mg[a]) | | |
|---|---|---|---|
| | LIP2 | LIP4 | CRL |
| p-NP acteate (C2) | 11 ± 1 (0.4)[b] | 10 ± 1 (0.7) | 16 ± 2 (3.1) |
| p-NP butyrate (C4) | 1986 ± 30 (72) | 899 ± 20 (63) | 359 ± 42 (72) |

TABLE 1-continued

Hydrolysis of p-nitrophenyl (p-NP) esters of various chain-length fatty acids.

| | (U/mg$^a$) | | |
|---|---|---|---|
| | LIP2 | LIP4 | CRL |
| p-NP caproate (C6) | 108 ± 15 (4) | 151 ± 13 (11) | 72 ± 5 (14) |
| p-NP caprylate (C8) | 978 ± 126 (35) | 504 ± 24 (35) | 498 ± 67 (100) |
| p-NP caprate (C10) | 1453 ± 210 (53) | 1295 ± 179 (91) | 395 ± 19 (79) |
| p-NP laurate (C12) | 2567 ± 277 (93) | 867 ± 41 (61) | 269 ± 44 (54) |
| p-NP myristate (C14) | 2567 ± 277 (93) | 1140 ± 41 (80) | 372 ± 5 (75) |
| p-NP palmitate (C16) | 2766 ± 4 (100) | 1429 ± 127 (100) | 317 ± 5 (64) |
| p-NP stearate (C18) | 1580 ± 21 (57) | 580 ± 21 (41) | 67 ± 1 (13) |

$^a$The unit (U) definition: One unit of activity is the amount of enzyme necessary to hydrolyze 1.0 micromole of p-nitrophenyl ester per min at 37° C. and pH 7.0.
$^b$The parentheses represent the ratio of the activity of each substrate to the highest one for the same enzyme.

TABLE 2

Hydrolysis of triglyceride of various chain-length fatty acids.

| | (U/mg$^a$) | | |
|---|---|---|---|
| | LIP2 | LIP4 | CRL |
| Triacetin (C2) | 39 ± 1 (2)$^b$ | 10 ± 1 (0) | 11 ± 1 (0) |
| Tribytyrin (C4) | 2540 ± 60 (100) | 1138 ± 10 (28) | 1029 ± 64 (33) |
| Tricaproin (C6) | 599 ± 37 (24) | 167 ± 7 (4) | 358 ± 14 (11) |
| Tricaprylin (C8) | 1239 ± 31 (49) | 4082 ± 298 (100) | 3118 ± 190 (100) |
| Tricaprin (C10) | 1399 ± 176 (55) | 628 ± 11 (15) | 2160 ± 75 (69) |
| Trilaurin (C12) | 1743 ± 110 (69) | 389 ± 4 (10) | 1502 ± 8 (48) |
| Trimyristin (C14) | 504 ± 33 (20) | 375 ± 33 (9) | 915 ± 26 (29) |
| Tripalmitin (C16) | 54 ± 6 (2) | 151 ± 10 (4) | 137 ± 12 (4) |
| Tristearin (C18) | 422 ± 9 (17) | 348 ± 38 (9) | 39 ± 2 (1) |
| Triolein (C18:1) | 513 ± 4 (20) | 352 ± 5 (9) | 303 ± 24 (10) |

$^a$The unit (U) definition: One unit of activity is the amount of enzyme necessary to hydrolyze 1.0 micromole of ester bond per min at 37° C. and pH 7.0.
$^b$The parentheses represent the ratio of the activity of each substrate to the highest one for the same enzyme.

TABLE 3

Hydrolysis of cholesterol esters of various chain-length fatty acids.

| | ($10^{-2}$U/mg$^a$) | | |
|---|---|---|---|
| | LIP2 | LIP4 | CRL |
| Cholesteryl n-butyrate (C4) | 127.1 ± 1.4 (32)$^b$ | 24.7 ± 1.3 (25) | 7.3 ± 0.1 (53) |
| Cholesteryl laurate (C12) | 402.0 ± 35.5 (100) | 98.2 ± 3.2 (100) | 13.8 ± 0.5 (100) |
| Cholesteryl stearate (C18) | 127.1 ± 1.4 (32) | 45.0 ± 1.8 (46) | 6.5 ± 0.7 (47) |

$^a$The unit (U) definition: One unit of activity is the amount of enzyme necessary to hydrolyze 1.0 micromole of cholesteryl ester per min at 37° C. and pH 7.0.
$^b$The parentheses represent the ratio of the activity of each substrate to the highest one for the same enzyme.

TABLE 4

Esterification of myristic acid with various chain-length alcohols.

| | ($10^3$ μmol/h/mg)$^a$ | | |
|---|---|---|---|
| | LIP2 | LIP4 | CRL |
| n-hexyl myristate | 1.86 ± 0.17 (57)$^b$ | 2.35 ± 0.24 (100) | 3.89 ± 0.47 (100) |
| n-octyl myristate | 2.28 ± 0.27 (70) | 1.55 ± 0.16 (66) | 2.73 ± 0.30 (70) |
| n-dodecyl myristate | 1.16 ± 0.11 (35) | 0.66 ± 0.07 (28) | 1.79 ± 0.20 (46) |
| n-hexadecyl myristate | 2.33 ± 0.22 (72) | 1.04 ± 0.08 (44) | 1.13 ± 0.13 (29) |
| n-octadecyl myristate | 3.26 ± 0.33 (100) | 1.71 ± 0.11 (72) | 1.19 ± 0.07 (31) |

$^a$Initial rate of reaction in the esterification of myristic acid with equimolar mixtures of different chain-length alkyl alcohols catalyzed by recombinant and a commercial CRLs.
$^b$The parentheses represent the ratio of the activity of each substrate to the highest one for the same enzyme.

TABLE 5

Esterfication of various chain-length acids with n-propanol.

| | ($10^3$ μmol/h/mg)[a] | | |
|---|---|---|---|
| | LIP2 | LIP4 | CRL |
| n-propyl butyrate | 9.96 ± 1.04 (100)[b] | 5.19 ± 0.49 (100) | 0.95 ± 0.05 (99) |
| n-propyl octanoate | 2.41 ± 0.24 (24) | 2.35 ± 0.11 (45) | 0.68 ± 0.05 (70) |
| n-propyl dodecanoate | 1.10 ± 0.13 (11) | 1.35 ± 0.06 (26) | 0.43 ± 0.05 (45) |
| n-propyl hexadecanoate | 0.68 ± 0.07 (7) | 1.56 ± 0.21 (30) | 0.96 ± 0.12 (100) |
| n-propyl octadecanoate | 0.77 ± 0.02 (8) | 1.01 ± 0.06 (19) | 0.94 ± 0.12 (98) |

[a]Initial rate of reaction in the esterification of n-propanol with equimolar mixtures of various chain-length fatty acids catalyzed by recombinant and commercial CRLs.
[b]The parentheses represent the ratio of the activity of each substrate to the highest one for the same enzyme.

Expression of Chimeric Proteins

Material and Methods

Construction of expression vectors The *E. coli* expression vectors pET23a-LIP4-S19 and pET23a-trx-LIP4-S19 were constructed as described in Tang et al. (2000) *Protein Exp. Purif.* 20: 308–313. Open-reading frames of LIP1, LIP2, LIP3, and LIP5 without the leader sequence were obtained by reverse transcription-polymerase chain reaction (RT-PCR). See Longhi et al. (1992) *Biochim. Biophy. Acta* 1131:227–232; and Lotti et al (1993) *Gene* 124:44–55. The chimeric DNA sequences were constructed by replacing the SphI(184)-BstXI(304) restriction DNA fragment of LIP4 with the corresponding fragments of LIP1, LIP2, LIP3, or LIP5, respectively. The resulting sequences encode mature chimeric *C. rugosa* lipases, denoted as TrX-LIP4/lid1, TrX-LIP4/lid2, TrX-LIP4/lid3, and TrX-LIP4/lid5, and were confirmed by DNA sequencing.

Preparation of recombinant LIP4 from *E. coli*. *E. coli* strain AD494(DE3) (Novagen, Milwaukee, Wis.) harboring recombinant plasmid was grown overnight at 37° C. in Luria-Bertani (LB) broth supplemented with 50 μg/mL ampicillin and 15 μg/mL kanamycin. The cells were then diluted 20-fold into fresh medium and incubated with shaking at 25° C. After adding IPTG to give a final concentration of 0.05 mM, the cells were incubated at 10° C. until $OD_{600}$ reached 1.0.

Purification of recombinant LIP4. After induction, the AD494(DE3) transformants were harvested by centrifugation at 4000g and 4° C. for 10 min. The cell pellet was resuspended in TE buffer (20 mM Tris-HCl and 2.5 mM EDTA, pH 8.0). The cells were disrupted with a sonicator, and the soluble fractions of the cell lysates were then collected by centrifugation at 15,000g at 4° C. for 30 min. The soluble fractions were concentrated by ultrafiltration on a 10,000 molecular weight cut-off membrane. These samples were then applied onto a DEAE-Sepharose CL-6B (Pharmacia Biotech) column equilibrated with TE buffer. Recombinant lipases were eluted using a linear gradient of 0 to 100 mM $(NH_4)_2SO_4$ over 5 column volumes.

The eluted proteins were then applied to a Butyl-Sepharose 4 Fast Flow (Pharmacia Biotech) hydrophobic interaction column. The column was washed with 5 bed volumes of TE buffer plus 1 mM and then 4 mM CHAPS. Bound proteins were then eluted with 5 bed volumes of TE buffer containing 30 mM CHAPS. The eluted samples were dialyzed against TE buffer and stored in a storage buffer (60 mM KCl, 10 mM Tris-HCl, 1.25 mM EDTA, 1% Triton X-100, and 17% glycerol, pH 7.5) at −20° C. Protein concentrations in the fractions were measured with the Bio-Rad assay kit, and esterase activity was determined using p-nitrophenyl butyrate as a substrate. The molecular masses of the purified recombinant lipases and a commercial lipase (Lipase Type VII, Sigma L1754) were determined by SDS-PAGE analysis.

Chimeric protein expression. A chimeric protein, its substrate interacting domain exchanged with one of another isomer, was prepared as described above.

Enzyme assay. Lipase activities were measured by titrimetry using tributyrin as substrates. The release of free fatty acid was continuously monitored by titration with 10 mM NaOH on the pH-Stat. The esterase activity at 37° C. was determined spectrophotometrically using p-nitrophenyl esters as substrates. One unit of activity was defined as the amount of enzyme that is able to release 1 μmol of p-nitrophenol per minute.

Results

To improve the protein solubility and facilitate the purification, the *E. coli* thioredoxin (Trx) was fused to the N-terminal of LIP4 to produce fusion protein Trx-LIP4. The Trx-LIP4 had better solubility and retained activity similar to native LIP4. Although the pairwise identities of overall amino acid sequence of LIP1, LIP2, LIP3 and LIP5, compared with LIP4, were 81, 83, 84 and 78%, respectively, but the substrate interacting domain (i.e., lid region) amino acid identities were 50, 53, 50 and 56% (Table 6), respectively.

To study the effect of the lid region on lipase activity and specificity, lid regions from the other four *C. rugosa* isoforms (LIP1, 2, 3, and 5; and corresponding lids 1, 2, 3, and 5) were exchanged with that of LIP4 and expressed as chimeric proteins Trx-LIP4/lid1, Trx-LIP4/lid2, Trx-LIP4/lid3 and Trx-LIP4/lid5, respectively. As shown in Table 7, the lipase hydrolysis activities of Trx-LIP4/lid2 and Trx-LIP4/lid3 increased 14% and 32%, respectively, whereas Trx-LIP4/lid1 and Trx-LIP4/lid5 decreased 85% and 20%, respectively, compared with native LIP4 with tributyrin as a substrate.

The effect of lid on lipase specificity depended greatly on which substrate was used. As shown in Table 8, although all the chimeric proteins with lid changes showed decreases in activity to varying extents, compared with native Trx-LIP4, the relative activities for various cholesterol esters of different chain length fatty acids showed substantial changes. For example, the best substrate for Trx-LIP4, Trx-LIP4/lid2 and Trx-LIP4/lid3 is cholesterol caprate, but the best for Trx-LIP4/lid1 and Trx-LIP4/lid5 is cholesterol stearate. In contrast, when p-nitrophenyl esters were used as substrates, both p-nitrophenyl caprate and stearate were the best substrates for Trx-LIP4 and Trx-LIP2, whereas only p-nitrophenyl caprate was the best substrate for Trx-LIP4/lid1, Trx-LIP4/lid3 and Trx-LIP4/lid5. The lid change also affected the substrate specificity of enzymes on the selectivity of cholesterol esters of various desaturated fatty acids. As shown in Table 9, the cholesteryl oleate (18:1) was the best substrate for Trx-LIP4, followed by cholesteryl linoleate (18:2, relative activity 68%), whereas cholesteryl stearate (18:0) was a poor substrate (relative activity 7%). Trx-LIP4/lid2 and Trx-LIP4/lid3 had a similar substrate preference pattern.

Further, the best substrate for Trx-LIP4/lid1 was cholesteryl stearate, followed by cholesteryl linoleate and then cholesteryl oleate. For Trx-LIP4/lid5, the substrate preference order was cholesteryl oleate, cholesteryl stearate, and cholesteryl linoleate. The kinetic parameters of various recombinant LIP4 chimeric proteins with cholesteryl linoleate were analyzed. As shown in Table 10, the fusion protein Trx-LIP4 showed a kcat/Km similar to native LIP4 although both Vmax and Km were increased. Trx-LIP4/lid2 retained a catalytic efficiency similar to Trx-LIP4, whereas Trx-LIP4/lid1, Trx-LIP4/lid3 and Trx-LIP4/lid5 showed greatly decreased kcat/Km. The decrease in the catalytic efficiency appeared due to the great decrease in kcat.

The lid domain also affected the enantioselectivity of lipase. As shown in Table 11, the *C. rugosa* lipase favored the hydrolysis of l-menthyl acetate over d-menthyl acetate. The recombinant Trx-LIP4 and all the chimeric LIP4 showed much better enantioselectivities than a commercial *C. rugosa* lipase (Lipase Type VII, Sigma). Only the enantioselectivity of Trx-LIP4/lid3 was similar to Trx-LIP4. Other chimeric proteins (Trx-LIP4/lid1, Trx-LIP4/lid2 and Trx-LIP4/lid5) showed substantial decreases in enantioselectivity with methyl acetate as a substrate. The enantioselectivity preference order might quite possibly change if other chiral substrates were used.

What is the structural basis of the lid domain effect on lipase catalysis? From computer analysis, positively charged Lys75 in the lid domain of native LIP4 (lid4) formed a hydrogen bonding and an electrostatic interaction with negatively charged Asp292, residing on the protein surface, to stabilize the lid4 in the open form conformation (an active state of lipase for hydrophobic substrates). Therefore this contributed to the high activity of LIP4 toward hydrophobic substrates such as medium and long chain fatty acid esters (Table 8–10). The lid2 domain has a lid conformation and amino acid residues similar to the lid4 in stabilizing the open form conformation (Table 6), and therefore the Trx-LIP4/lid2 chimeric protein showed a catalytic efficiency close to that of Trx-LIP4. In contrast, the Lys75-Asp292 interactions were disturbed by Glu71 in lid1, 3, and 5, and therefore these chimeric proteins showed great decreases in catalytic efficiency for hydrophobic substrates.

For short chain hydrophilic substrates, the effect of this open form stabilization is less important. Thus, the even better lipase activity of Trx-LIP4/lid3 for tributyrin hydrolysis than Trx-LIP4 (Table 7) might be due to the different conformations of active sites or substrate binding sites. Likewise, Trx-LIP4/lid3 showed a similar enantioselectivity to Trx-LIP4 (Table 11), and might assumed a similar catalytic machinery setting the chiral enantiopreference toward second alcohols. See Cygler et al. (1994) *J. Am. Chem. Soc.* 116: 3180–3186. In these cases, the effect of lid domain exchange could have been due to conformational changes, which had a subtle effect on the active site region and led to changes in substrate specificity and catalytic efficiency.

In conclusion, the lid domain has a significant effect on recombinant LIP enzyme catalytic efficiency, on the fatty acid chain length and desaturation selectivity of ester substrates, and on enantioselectivity. Therefore, the lid domain is a good choice for protein engineering to rationally design the biocatalytic properties of *C. rugosa* lipase for desired industrial applications. Site-directed mutagenesis on the lid region of LIP4 is currently underway to pinpoint the amino acid residues responsible for the substrate specificity, catalytic efficiency, enantioselectivity, and possibly enzyme stability.

TABLE 6

Comparison of overall and lid domain amino acid sequence identity of five *C. rugosa* lipase isoforms. Sequences were aligned by the CLUSTAL W program.

Pairwise identity (similarity) percentage of the full-length LIP proteins (534 aa).

|      | LIP1      | LIP2     | LIP3     | LIP4     | LIP5     |
|------|-----------|----------|----------|----------|----------|
| LIP1 | 100 (100) | 80 (89)  | 88 (95)  | 81 (90)  | 82 (92)  |
| LIP2 |           | 100 (100)| 82 (89)  | 83 (91)  | 77 (88)  |
| LIP3 |           |          | 100 (100)| 84 (91)  | 86 (94)  |
| LIP4 |           |          |          | 100 (100)| 78 (90)  |
| LIP5 |           |          |          |          | 100 (100)|

Among five sequences: identity = 66%; similarity = 81%.

Pairwise identity (similarity) percentage of the changed lid domains (residue 63–94) of the wild type and chimeric LIP4.

|      | lid1      | lid2      | lid3      | lid4      | lid5      |
|------|-----------|-----------|-----------|-----------|-----------|
| lid1 | 100 (100) | 56 (75)   | 81 (91)   | 50 (72)   | 88 (91)   |
| lid2 |           | 100 (100) | 63 (78)   | 53 (81)   | 66 (81)   |
| lid3 |           |           | 100 (100) | 50 (75)   | 88 (94)   |
| lid4 |           |           |           | 100 (100) | 56 (75)   |
| lid5 |           |           |           |           | 100 (100) |

Among five sequences: identity = 37.5%; similarity = 62.5%.

TABLE 7

Lipase activity of recombinant LIP4 expressed in *E. coli*

| Enzyme        | Specific activity ($10^3$ U/mg)[a] | Relative activity (%)[b] |
|---------------|-----------------------------------|--------------------------|
| Trx-LIP4      | 6.76                              | 100.0                    |
| Trx-LIP4/lid1 | 1.03                              | 15.2                     |
| Trx-LIP4/lid2 | 7.71                              | 114.2                    |
| Trx-LIP4/lid3 | 8.90                              | 131.7                    |
| Trx-LIP4/lid5 | 5.37                              | 79.5                     |

[a] One lipase unit (U) is defined as the enzyme amount which produces 1.0 micromole of butyric acid from tributyrin per min at pH 7.0 and 37° C.
[b] Relative activity is the ratio of the activity of each enzyme to that of the wild type LIP4.

TABLE 8

Hydrolysis of cholesterol esters and p-nitrophenyl esters of various chain-length fatty acids.

| Enzyme | Cholesterol esterase activity ($10^{-2}$ U/mg)[a] | | | p-Nitrophenol esterase activity (U/mg)[a] | | |
|---|---|---|---|---|---|---|
| | butyrate | caprate | stearate | butyrate | caprate | stearate |
| Trx-LIP4 | 6.2 (10)[b] | 62.2 (100) | 24.9 (40) | 12.5 (44) | 28.5 (100) | 28.2 (99) |
| Trx-LIP4/lid1 | 0.0 (0) | 3.7 (78) | 4.8 (100) | 0.7 (17) | 5.1 (100) | 0.6 (11) |
| Trx-LIP4/lid2 | 4.4 (9) | 47.7 (100) | 22.4 (47) | 7.3 (26) | 27.9 (100) | 26.9 (97) |
| Trx-LIP4/lid3 | 0.8 (6) | 14.5 (100) | 8.9 (61) | 1.2 (6) | 18.6 (100) | 5.0 (27) |
| Trx-LIP4/lid5 | 0.8 (11) | 6.4 (89) | 7.3 (100) | 0.5 (5) | 9.4 (100) | 1.0 (11) |

[a]One unit of activity(U) is the amount of enzyme necessary to hydrolyze 1.0 micromole of cholesteryl ester or p-nitrophenol ester per min at 37° C. and pH 7.0.
[b]Parentheses represent the ratio of the activity of each substrate to the highest one for the same enzyme.

TABLE 9

Hydrolysis of cholesterol esters of various unsaturated fatty acids.

| Enzyme | Cholesterol esterase activity ($10^{-2}$ U/mg)[a] | | |
|---|---|---|---|
| | cholesteryl stearate (18:0) | cholesteryl oleate (18:1) | cholesteryl linoleate (18:1) |
| Trx-LIP4 | 24.9 (7)[b] | 354.6 (100) | 242.0 (68) |
| Trx-LIP4/lid1 | 4.8 (100) | 1.5 (32) | 2.5 (53) |
| Trx-LIP4/lid2 | 22.4 (9) | 244.7 (100) | 148.9 (61) |
| Trx-LIP4/lid3 | 8.9 (43) | 20.7 (100) | 18.6 (90) |
| Trx-LIP4/lid5 | 7.3 (85) | 8.5 (100) | 6.5 (76) |

[a]One unit of activity (U) is defined as the amount of enzyme necessary to hydrolyze 1.0 micromole of cholesteryl linoleate per minute at 37° C. and pH 7.0.
[b]The parentheses represent the ratio of the activity of each substrate to the highest one for the same enzyme.

TABLE 11

The enantioselectivity of recombinant LIP4s expressed in *E.coli* and a commercial lipase (CRL) with (d)- and (l)-menthyl acetate as substraes.

| Enzyme | v(l)[a] (umol/h/mg) | v(d) (umol/h/mg) | Enantioselectivity[b] v(l)/v(d) |
|---|---|---|---|
| Trx-LIP4 | 53.65 ± 4.10 | 1.69 ± 0.13 | 31.73 |
| Trx-LIP4/lid1 | 2.15 ± 0.18 | 0.40 ± 0.06 | 5.35 |
| Trx-LIP4/lid2 | 33.00 ± 3.48 | 2.89 ± 0.45 | 11.41 |
| Trx-LIP4/lid3 | 54.11 ± 3.10 | 1.70 ± 0.23 | 31.81 |
| Trx-LIP4/lid5 | 6.02 ± 0.57 | 0.48 ± 0.06 | 12.59 |
| CRL | 53.58 ± 3.38 | 42.65 ± 7.67 | 1.26 |

[a]Specific activity (v) is defined as the amount of (d)- or (l)-menthol released per mg of enzyme per hour at 30° C. and pH 7.0.

TABLE 10

Kinetic parameters of a hydrolysis reaction using cholesteryl linoleate as the substrate.

| Enzyme | $M_r$ | $V_{max}$ $10^{-3}$ μmol/min/mg | $K_m$ $10^{-3}$ mM | $k_{cat}$ $min^{-1}$ | $k_{cat}/K_m$ $mM^{-1}$ $min^{-1}$ |
|---|---|---|---|---|---|
| Trx-LIP4 | 69680 | 2895 ± 117 | 104 ± 10 | 202 ± 8.12 | 1940 ± 139 |
| LIP4 | 57051 | 1235 ± 32 | 41 ± 5 | 70 ± 0.17 | 1740 ± 298 |
| Trx-LIP4/lid1 | 69717 | 28 ± 1 | 103 ± 5 | 2 ± 0.04 | 19 ± 0.47 |
| Trx-LIP4/lid2 | 69877 | 1851 ± 24 | 74 ± 3 | 129 ± 0.22 | 1751 ± 64 |
| Trx-LIP4/lid3 | 69757 | 231 ± 14 | 46 ± 1 | 16 ± 0.17 | 349 ± 7 |
| Trx-LIP4/lid5 | 69797 | 70 ± 4.8 | 34 ± 1 | 5 ± 0.01 | 147 ± 3 |

[a]The assay temperature was 37° C. and pH was 7.0. The concentrations of Trx-LIP4, LIP4, Trx-LIP4/lid1, Trx-LIP4/lid2, Trx-LIP4/lid3 and Trx-LIP4/lid5 were 29 nM, 39 nM, 11 nM, 86 nM, 58 nM and 66 nM, respectively. The values are averages from three independent experiments.
[b]The molecular weights of the recombinant proteins were predicted from the deduced amino acid sequences and those of commercial enzymes were determined from SDS_PAGE.

OTHER EMBODIMENT

All of the features disclosed in this specification may be combined in any combination. Each feature disclosed in this specification may be replace by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated nucleic acid comprising a mutant DNA encoding a variant *Candida rugosa* lipase having at least 98% identity to SEQ ID NO: 4, wherein the mutant DNA is at least 80% identical to a *Candida rugosa* DNA encoding said lipase which is expressed in *Candida rugosa*, and wherein said mutant DNA has at least 15 CTG codons substituted by codons selected from the group consisting of TCT, TCC, TCA, TCG, AGT, and AGC in the DNA.

2. The nucleic acid of claim 1, wherein all CTG codons of said *Candida rugosa* DNA are substituted by codons selected from the group consisting of TCT, TCC, TCA, TCG, AGT, and AGC.

3. The nucleic acid of claim 2, wherein the amino acid sequence of the variant *Candida rugosa* lipase is SEQ ID NO: 4.

4. The nucleic acid of claim 1, wherein the mutant DNA is at least 85% identical to said *Candida rugosa* DNA.

5. The nucleic acid of claim 4, wherein the amino acid sequence of the variant *Candida rugosa* lipase is SEQ ID NO: 4.

6. The nucleic acid of claim 1, wherein the mutant DNA is at least 90% identical to the *Candida rugosa* DNA.

7. The nucleic acid of claim 6, wherein the amino acid sequence of the variant *Candida rugosa* lipase is SEQ ID NO: 4.

8. The nucleic acid of claim 1, wherein the mutant DNA is at least 95% identical to said *Candida rugosa* DNA.

9. The nucleic acid of claim 8, wherein the amino acid sequence of the variant *Candida rugosa* lipase is SEQ ID NO: 4.

10. The nucleic acid of claim 1, where in the variant *Candida rugosa* lipase has 100% identity to SEQ ID NO: 4.

11. A microorganism comprising the nucleic acid of claim 1, wherein the microorganism is a bacterium or a yeast.

12. The microorganism of claim 11, wherein the bacterium is *E. coli* and the yeast is *P. pastoris*.

13. The microorganism of claim 11, wherein the mutant DNA is at least 85% identical to said *Candida rugosa*.

14. The microorganism of claim 13, wherein the bacterium is *E. coil* and the yeast is *P. pastoris*.

15. The microorganism of claim 13, wherein the mutant DNA is at least 90% identical to said *Candida rugosa* DNA.

16. The microorganism of claim 15, wherein the mutant DNA is at least 95% identical to said *Candida rugosa* DNA.

17. The microorganism of claim 16, wherein wherein the amino acid sequence of the variant *Candida rugosa* lipase is SEQ ID NO: 4.

18. An isolated nucleic acid, comprising a DNA of SEQ ID NO: 3 or a degenerate variant thereof.

19. A method for preparing a mutant DNA encoding a *Candida rugosa* variant having at least 98% identity to the amino acid sequence of SEQ ID NO: 4, comprising:

(a) providing a DNA encoding a variant *Candida rugosa* lipase having at least 98% sequence identity to SEQ ID NO: 4; and (b) conducting PCR amplification by mixing said DNA of (a), a DNA polymerase, a pair of terminal primers for said DNA, and a number of pairs of internal, primers encompassing fragments of said DNA of (a), wherein each of the internal primers includes one or more of universal codons and anticodons for serine selected from the group consisting of TCT, TCC, TCA, TCG, AGT, AGC, AGA, GGA, TGA, CGA, ACT, and GCT, in which the universal codons and anticodons substituted for at least 15 CTG codons in the DNA of (a); and each internal primer overlaps with another internal or terminal primer in a manner that a mutant DNA encoding the variant *Candida rugosa* lipase is obtained by amplification.

20. The method of claim 19, wherein all codons correspond to CTG codons in said *Candida rugosa* DNA of (a) are substituted by codons selected from the group consisting of TCT, TCC, TCA, TCG, AGT, and AGC.

21. The method of claim 19, wherein the amino acid sequence of the variant *Candida rugosa* lipase is SEQ ID NO: 4.

22. The method of claim 19, wherein the mutant DNA is SEQ ID NO: 3 or a degenerate variant *thereof*.

* * * * *

SEQUENCE LISTING

```
<160> NUMBER OF SEQ ID NOS: 11

<210> SEQ ID NO 1
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 1 tcg atg aat tca cgt ggc cca gcc ggc cgt ctc gga tcg gta ccc acc      48
Ser Met Asn Ser Arg Gly Pro Ala Gly Arg Leu Gly Ser Val Pro Thr
 1               5                  10                  15 gcc acg ctc gcc aac ggc gac acc atc acc ggt ctc aac gcc att gtc      96
Ala Thr Leu Ala Asn Gly Asp Thr Ile Thr Gly Leu Asn Ala Ile Val
             20                  25                  30 aac gaa aag ttt ctc ggc ata ccg ttt gcc gag ccg ccc gtg ggc agc     144
Asn Glu Lys Phe Leu Gly Ile Pro Phe Ala Glu Pro Pro Val Gly Ser
         35                  40                  45 ctc cgc ttc aag ccg ccc gtg ccg tac tcg gcg tcg ctc aac ggc cag     192
Leu Arg Phe Lys Pro Pro Val Pro Tyr Ser Ala Ser Leu Asn Gly Gln
     50                  55                  60 cag ttt acc tct tac ggc ccg tct tgc atg cag atg aac cct atg ggc     240
Gln Phe Thr Ser Tyr Gly Pro Ser Cys Met Gln Met Asn Pro Met Gly
 65                  70                  75                  80 tcg ttt gag gac aca ctt ccc aag aat gcg ctt gac ttg gtg ctc cag     288
Ser Phe Glu Asp Thr Leu Pro Lys Asn Ala Leu Asp Leu Val Leu Gln
                 85                  90                  95 tcc aag atc ttc caa gtg gtg ctt ccc aac gac gag gac tgt ctc acc     336
Ser Lys Ile Phe Gln Val Val Leu Pro Asn Asp Glu Asp Cys Leu Thr
            100                 105                 110 atc aac gtg atc cgg ccg ccc ggc acc agg gcc agt gct ggt ctc ccg     384
Ile Asn Val Ile Arg Pro Pro Gly Thr Arg Ala Ser Ala Gly Leu Pro
        115                 120                 125 gtg atg ctc tgg atc ttt ggc ggt ggg ttt gag ctt ggc ggc tcc agc     432
Val Met Leu Trp Ile Phe Gly Gly Gly Phe Glu Leu Gly Gly Ser Ser
    130                 135                 140 ctc ttt cca gga gac cag atg gtg gcc aag agc gtg ctc atg ggt aaa     480
Leu Phe Pro Gly Asp Gln Met Val Ala Lys Ser Val Leu Met Gly Lys
145                 150                 155                 160 ccg gtg atc cac gtg agc atg aac tac cgc gtg gcg tca tgg ggg ttc     528
Pro Val Ile His Val Ser Met Asn Tyr Arg Val Ala Ser Trp Gly Phe
                165                 170                 175 ttg gcc ggc ccc gac atc cag aac gaa ggc agc ggg aac gcc ggc ttg     576
Leu Ala Gly Pro Asp Ile Gln Asn Glu Gly Ser Gly Asn Ala Gly Leu
            180                 185                 190 cat gac cag cgc ttg gcc atg cag tgg gtg gcg gac aac att gct ggg     624
His Asp Gln Arg Leu Ala Met Gln Trp Val Ala Asp Asn Ile Ala Gly
        195                 200                 205 ttt ggc ggc gac ccg agc aag gtg acc ata tac ggc gag tct gcg ggc     672
Phe Gly Gly Asp Pro Ser Lys Val Thr Ile Tyr Gly Glu Ser Ala Gly
```

```
                    210                     215                     220
agc atg tcg acg ttt gtg cac ctt gtg tgg aac gac ggc gac aac acg       720
Ser Met Ser Thr Phe Val His Leu Val Trp Asn Asp Gly Asp Asn Thr
225                 230                     235                 240 tac aac ggc aag ccg ttg ttc cgc gcc gcc atc atg cag tct ggc tgc       768
Tyr Asn Gly Lys Pro Leu Phe Arg Ala Ala Ile Met Gln Ser Gly Cys
                245                     250                     255 atg gtg ccg tct gac ccg gtg gac ggc acg tac ggc acc gag atc tac       816
Met Val Pro Ser Asp Pro Val Asp Gly Thr Tyr Gly Thr Glu Ile Tyr
            260                     265                     270 aac cag gtg gtg gcg tct gcc ggg tgt ggc agt gcc agc gac aag ctc       864
Asn Gln Val Val Ala Ser Ala Gly Cys Gly Ser Ala Ser Asp Lys Leu
        275                     280                     285 gcg tgc ttg cgc ggc ctt tct cag gac acg ttg tac cag gcc acg agc       912
Ala Cys Leu Arg Gly Leu Ser Gln Asp Thr Leu Tyr Gln Ala Thr Ser
    290                     295                     300 gac acg ccc ggc gtg ttg gcg tac ccg tcg ttg cgg ttg tct tat ctc       960
Asp Thr Pro Gly Val Leu Ala Tyr Pro Ser Leu Arg Leu Ser Tyr Leu
305                     310                     315                 320 ccg cgg ccc gac ggc acc ttc atc acc gac gac atg tat gcc ttg gtg      1008
Pro Arg Pro Asp Gly Thr Phe Ile Thr Asp Asp Met Tyr Ala Leu Val
                325                     330                     335 cgg gac ggc aag tac gca cac gtg ccg gtg atc atc ggc gac cag aac      1056
Arg Asp Gly Lys Tyr Ala His Val Pro Val Ile Ile Gly Asp Gln Asn
            340                     345                     350 gac gag ggc act ttg ttt ggg ctc tct tct ttg aac gtg acc aca gat      1104
Asp Glu Gly Thr Leu Phe Gly Leu Ser Ser Leu Asn Val Thr Thr Asp
        355                     360                     365 gct cag gca cgg gcg tac ttc aag cag tct ttc atc cac gcc agc gat      1152
Ala Gln Ala Arg Ala Tyr Phe Lys Gln Ser Phe Ile His Ala Ser Asp
    370                     375                     380 gcg gag atc gac acg ttg atg gcg gcg tac acc agc gac atc acc cag      1200
Ala Glu Ile Asp Thr Leu Met Ala Ala Tyr Thr Ser Asp Ile Thr Gln
385                     390                     395                 400 ggt tct ccg ttc gac acc ggc atc ttc aat gcc atc acc ccg cag ttc      1248
Gly Ser Pro Phe Asp Thr Gly Ile Phe Asn Ala Ile Thr Pro Gln Phe
                405                     410                     415 aaa cgg atc tct gcg ttg ctt ggc gac ctt gcg ttc acg ctt gcg cgt      1296
Lys Arg Ile Ser Ala Leu Leu Gly Asp Leu Ala Phe Thr Leu Ala Arg
            420                     425                     430 cgc tac ttc ctc aac tac tac cag ggc ggc acc aag tac tcg ttc ctc      1344
Arg Tyr Phe Leu Asn Tyr Tyr Gln Gly Gly Thr Lys Tyr Ser Phe Leu
        435                     440                     445 tct aag cag ctt tct ggg ttg ccc gtc ttg ggc acc ttc cac ggc aac      1392
Ser Lys Gln Leu Ser Gly Leu Pro Val Leu Gly Thr Phe His Gly Asn
    450                     455                     460 gac atc atc tgg cag gac tac ttg gtg ggc agc ggc agt gtg atc tac      1440
Asp Ile Ile Trp Gln Asp Tyr Leu Val Gly Ser Gly Ser Val Ile Tyr
465                     470                     475                 480 aac aac gcg ttc att gcg ttt gcc aac gac ctc gac ccg aac aag gcg      1488
Asn Asn Ala Phe Ile Ala Phe Ala Asn Asp Leu Asp Pro Asn Lys Ala
                485                     490                     495 ggc ttg tgg acc aac tgg ccc acg tac acc agc agc tct cag tct ggc      1536
Gly Leu Trp Thr Asn Trp Pro Thr Tyr Thr Ser Ser Ser Gln Ser Gly
            500                     505                     510 aac aac ttg atg cag atc aac ggc ttg ggg ttg tac acc ggc aag gac      1584
Asn Asn Leu Met Gln Ile Asn Gly Leu Gly Leu Tyr Thr Gly Lys Asp
        515                     520                     525 aac ttc cgc ccg gat gcg tac agc gcc ctc ttt tcc aac ccg ccg tct      1632
```

-continued

```
Asn Phe Arg Pro Asp Ala Tyr Ser Ala Leu Phe Ser Asn Pro Pro Ser
        530                 535                 540
ttc ttt gtg                                                              1641
Phe Phe Val
545

<210> SEQ ID NO 2
<211> LENGTH: 547
<212> TYPE: PRT
<213> ORGANISM: Candida rugosa

<400> SEQUENCE: 2

Ser Met Asn Ser Arg Gly Pro Ala Gly Arg Leu Gly Ser Val Pro Thr
  1               5                  10                  15

Ala Thr Leu Ala Asn Gly Asp Thr Ile Thr Gly Leu Asn Ala Ile Val
                 20                  25                  30

Asn Glu Lys Phe Leu Gly Ile Pro Phe Ala Glu Pro Pro Val Gly Ser
             35                  40                  45

Leu Arg Phe Lys Pro Pro Val Pro Tyr Ser Ala Ser Leu Asn Gly Gln
 50                  55                  60

Gln Phe Thr Ser Tyr Gly Pro Ser Cys Met Gln Met Asn Pro Met Gly
 65                  70                  75                  80

Ser Phe Glu Asp Thr Leu Pro Lys Asn Ala Leu Asp Leu Val Leu Gln
                 85                  90                  95

Ser Lys Ile Phe Gln Val Val Leu Pro Asn Asp Glu Asp Cys Leu Thr
            100                 105                 110

Ile Asn Val Ile Arg Pro Pro Gly Thr Arg Ala Ser Ala Gly Leu Pro
            115                 120                 125

Val Met Leu Trp Ile Phe Gly Gly Gly Phe Glu Leu Gly Gly Ser Ser
130                 135                 140

Leu Phe Pro Gly Asp Gln Met Val Ala Lys Ser Val Leu Met Gly Lys
145                 150                 155                 160

Pro Val Ile His Val Ser Met Asn Tyr Arg Val Ala Ser Trp Gly Phe
                165                 170                 175

Leu Ala Gly Pro Asp Ile Gln Asn Glu Gly Ser Gly Asn Ala Gly Leu
            180                 185                 190

His Asp Gln Arg Leu Ala Met Gln Trp Val Ala Asp Asn Ile Ala Gly
            195                 200                 205

Phe Gly Gly Asp Pro Ser Lys Val Thr Ile Tyr Gly Glu Ser Ala Gly
        210                 215                 220

Ser Met Ser Thr Phe Val His Leu Val Trp Asn Asp Gly Asp Asn Thr
225                 230                 235                 240

Tyr Asn Gly Lys Pro Leu Phe Arg Ala Ala Ile Met Gln Ser Gly Cys
                245                 250                 255

Met Val Pro Ser Asp Pro Val Asp Gly Thr Tyr Gly Thr Glu Ile Tyr
            260                 265                 270

Asn Gln Val Val Ala Ser Ala Gly Cys Gly Ser Ala Ser Asp Lys Leu
            275                 280                 285

Ala Cys Leu Arg Gly Leu Ser Gln Asp Thr Leu Tyr Gln Ala Thr Ser
        290                 295                 300

Asp Thr Pro Gly Val Leu Ala Tyr Pro Ser Leu Arg Leu Ser Tyr Leu
305                 310                 315                 320

Pro Arg Pro Asp Gly Thr Phe Ile Thr Asp Asp Met Tyr Ala Leu Val
                325                 330                 335

Arg Asp Gly Lys Tyr Ala His Val Pro Val Ile Ile Gly Asp Gln Asn
```

-continued

```
                 340                 345                 350
Asp Glu Gly Thr Leu Phe Gly Leu Ser Ser Leu Asn Val Thr Thr Asp
            355                 360                 365
Ala Gln Ala Arg Ala Tyr Phe Lys Gln Ser Phe Ile His Ala Ser Asp
    370                 375                 380
Ala Glu Ile Asp Thr Leu Met Ala Ala Tyr Thr Ser Asp Ile Thr Gln
385                 390                 395                 400
Gly Ser Pro Phe Asp Thr Gly Ile Phe Asn Ala Ile Thr Pro Gln Phe
                405                 410                 415
Lys Arg Ile Ser Ala Leu Leu Gly Asp Leu Ala Phe Thr Leu Ala Arg
            420                 425                 430
Arg Tyr Phe Leu Asn Tyr Tyr Gln Gly Gly Thr Lys Tyr Ser Phe Leu
    435                 440                 445
Ser Lys Gln Leu Ser Gly Leu Pro Val Leu Gly Thr Phe His Gly Asn
    450                 455                 460
Asp Ile Ile Trp Gln Asp Tyr Leu Val Gly Ser Gly Ser Val Ile Tyr
465                 470                 475                 480
Asn Asn Ala Phe Ile Ala Phe Ala Asn Asp Leu Asp Pro Asn Lys Ala
                485                 490                 495
Gly Leu Trp Thr Asn Trp Pro Thr Tyr Thr Ser Ser Gln Ser Gly
            500                 505                 510
Asn Asn Leu Met Gln Ile Asn Gly Leu Gly Leu Tyr Thr Gly Lys Asp
    515                 520                 525
Asn Phe Arg Pro Asp Ala Tyr Ser Ala Leu Phe Ser Asn Pro Pro Ser
    530                 535                 540
Phe Phe Val
545

<210> SEQ ID NO 3
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 3 tcg atg aat tca cgt ggc cca gcc ggc cgt ctc gga tcg gta ccc acc      48
Ser Met Asn Ser Arg Gly Pro Ala Gly Arg Leu Gly Ser Val Pro Thr
1               5                   10                  15 gcc aag ctc gcc aac ggc gac acc atc acc ggt ctc aac gcc atc atc      96
Ala Lys Leu Ala Asn Gly Asp Thr Ile Thr Gly Leu Asn Ala Ile Ile
                20                  25                  30 aac gag gcg ttc ctc ggc att ccc ttt gcc gag ccg ccg gtg ggc aac     144
Asn Glu Ala Phe Leu Gly Ile Pro Phe Ala Glu Pro Pro Val Gly Asn
            35                  40                  45 ctc cgc ttc aag gac cct gtg ccg tac tct ggc tcg ctc aac ggc cag     192
Leu Arg Phe Lys Asp Pro Val Pro Tyr Ser Gly Ser Leu Asn Gly Gln
    50                  55                  60 aag ttc act tct tac ggc ccg tct tgc atg cag cag aac ccc gag ggc     240
Lys Phe Thr Ser Tyr Gly Pro Ser Cys Met Gln Gln Asn Pro Glu Gly
65                  70                  75                  80 acg ttt gaa gag aac ctt ggc aag acg gca ctc gac ttg gtg atg cag     288
Thr Phe Glu Glu Asn Leu Gly Lys Thr Ala Leu Asp Leu Val Met Gln
                85                  90                  95 tcc aag gtg ttc cag gcg gtg ctt ccc cag agt gag gac tgc ctc acc     336
Ser Lys Val Phe Gln Ala Val Leu Pro Gln Ser Glu Asp Cys Leu Thr
                100                 105                 110
```

-continued

| | |
|---|---|
| atc aac gtg gtg cgg ccg ccg ggc acc aag gcg ggc gcc aac ctc ccg<br>Ile Asn Val Val Arg Pro Pro Gly Thr Lys Ala Gly Ala Asn Leu Pro<br>115                        120                      125 | 384 |
| gtc atg ctc tgg atc ttt ggc ggt ggg ttt gag atc ggc agc ccc acc<br>Val Met Leu Trp Ile Phe Gly Gly Gly Phe Glu Ile Gly Ser Pro Thr<br>130                        135                      140 | 432 |
| atc ttc cct ccc gcc cag atg gtc acc aag agt gtg ctc atg ggc aag<br>Ile Phe Pro Pro Ala Gln Met Val Thr Lys Ser Val Leu Met Gly Lys<br>145                        150                      155                      160 | 480 |
| cac atc atc cac gtg gcc gtc aac tac cgt gtt gcc tcg tgg ggg ttc<br>His Ile Ile His Val Ala Val Asn Tyr Arg Val Ala Ser Trp Gly Phe<br>                        165                      170                      175 | 528 |
| ttg gct ggt gat gac atc aag gcc gag ggc agc ggg aac gcc ggc ttg<br>Leu Ala Gly Asp Asp Ile Lys Ala Glu Gly Ser Gly Asn Ala Gly Leu<br>                  180                        185                      190 | 576 |
| aag gac cag cgt ttg ggc atg cag tgg gtg gca gac aac att gcc ggg<br>Lys Asp Gln Arg Leu Gly Met Gln Trp Val Ala Asp Asn Ile Ala Gly<br>                        195                      200                      205 | 624 |
| ttc ggc ggc gac ccg agc aag gtg act atc ttt ggc gag tct gcg ggc<br>Phe Gly Gly Asp Pro Ser Lys Val Thr Ile Phe Gly Glu Ser Ala Gly<br>210                        215                      220 | 672 |
| agc atg tcc gtg ttg tgc cac ctc atc tgg aac gac ggc gac aac acg<br>Ser Met Ser Val Leu Cys His Leu Ile Trp Asn Asp Gly Asp Asn Thr<br>225                        230                      235                      240 | 720 |
| tac aag ggc aag ccg ttg ttc cgc gcg ggc atc atg cag tct gga gcc<br>Tyr Lys Gly Lys Pro Leu Phe Arg Ala Gly Ile Met Gln Ser Gly Ala<br>                        245                      250                      255 | 768 |
| atg gtg ccg tct gac ccg gtg gac ggc acg tac ggc aac gag atc tac<br>Met Val Pro Ser Asp Pro Val Asp Gly Thr Tyr Gly Asn Glu Ile Tyr<br>                  260                        265                      270 | 816 |
| gac ctc ttt gtc tcg agt gct ggc tgt ggc agc gcc agc gac aag ctc<br>Asp Leu Phe Val Ser Ser Ala Gly Cys Gly Ser Ala Ser Asp Lys Leu<br>                        275                      280                      285 | 864 |
| gcg tgc ttg cgc agt gcg tct agc gac acc ttg ctc gat gcc acc aac<br>Ala Cys Leu Arg Ser Ala Ser Ser Asp Thr Leu Leu Asp Ala Thr Asn<br>290                        295                      300 | 912 |
| aac act cct ggg ttc ttg gcg tac tcc tcg ttg cgg ttg tct tat ctc<br>Asn Thr Pro Gly Phe Leu Ala Tyr Ser Ser Leu Arg Leu Ser Tyr Leu<br>305                        310                      315                      320 | 960 |
| ccg cgg ccc gac ggc aag aac atc acc gat gac atg tac aag ttg gtg<br>Pro Arg Pro Asp Gly Lys Asn Ile Thr Asp Asp Met Tyr Lys Leu Val<br>                        325                      330                      335 | 1008 |
| cgc gac ggc aag tat gca agc gtt ccc gtg atc att ggc gac cag aac<br>Arg Asp Gly Lys Tyr Ala Ser Val Pro Val Ile Ile Gly Asp Gln Asn<br>                  340                        345                      350 | 1056 |
| gac gag ggc acc atc ttt ggg ctc tct tct ttg aac gtg acc acg aat<br>Asp Glu Gly Thr Ile Phe Gly Leu Ser Ser Leu Asn Val Thr Thr Asn<br>                  355                        360                      365 | 1104 |
| gct cag gcc cgt gct tac ttc aag cag tct ttc atc cac gcc agc gac<br>Ala Gln Ala Arg Ala Tyr Phe Lys Gln Ser Phe Ile His Ala Ser Asp<br>370                        375                      380 | 1152 |
| gcg gag atc gac acc ttg atg gcg gcg tac ccc cag gac atc acc cag<br>Ala Glu Ile Asp Thr Leu Met Ala Ala Tyr Pro Gln Asp Ile Thr Gln<br>385                        390                      395                      400 | 1200 |
| ggt tct ccg ttc gac acg ggt gtt ctc aac gcc ctc acc ccg cag ttc<br>Gly Ser Pro Phe Asp Thr Gly Val Leu Asn Ala Leu Thr Pro Gln Phe<br>                  405                        410                      415 | 1248 |
| aag aga atc tct gcg gtg ctc ggc gac ctt gca ttc atc cac gcc cgc<br>Lys Arg Ile Ser Ala Val Leu Gly Asp Leu Ala Phe Ile His Ala Arg | 1296 |

-continued

```
                 420                 425                 430
cgc tac ttc ctc aac cac ttc cag ggc ggc acc aag tac tcg ttc ctc    1344
Arg Tyr Phe Leu Asn His Phe Gln Gly Gly Thr Lys Tyr Ser Phe Leu
        435                 440                 445 tct aag cag ctc tct ggg ttg cca atc atg ggc acc ttc cat gcc aac    1392
Ser Lys Gln Leu Ser Gly Leu Pro Ile Met Gly Thr Phe His Ala Asn
    450                 455                 460 gac att gtg tgg cag gac tac ttg ttg gga agc ggc agc gtc atc tac    1440
Asp Ile Val Trp Gln Asp Tyr Leu Leu Gly Ser Gly Ser Val Ile Tyr
465                 470                 475                 480 aac aac gcg ttt atc gcg ttc gcc acc gac ttg gac ccc aac acc gcg    1488
Asn Asn Ala Phe Ile Ala Phe Ala Thr Asp Leu Asp Pro Asn Thr Ala
                485                 490                 495 ggg ttg ttg gtg aac tgg ccc aag tac acc agc agc tct cag tct ggc    1536
Gly Leu Leu Val Asn Trp Pro Lys Tyr Thr Ser Ser Ser Gln Ser Gly
            500                 505                 510 aac aac ttg atg atg atc aac gcc ttg ggc ttg tac acc ggc aag gac    1584
Asn Asn Leu Met Met Ile Asn Ala Leu Gly Leu Tyr Thr Gly Lys Asp
        515                 520                 525 aac ttc cgc acc gct ggc tac gac gcg ttg atg acc aac ccg tct tct    1632
Asn Phe Arg Thr Ala Gly Tyr Asp Ala Leu Met Thr Asn Pro Ser Ser
    530                 535                 540 ttc ttt gtg                                                         1641
Phe Phe Val
545
```

<210> SEQ ID NO 4
<211> LENGTH: 547
<212> TYPE: PRT
<213> ORGANISM: Candida rugosa

<400> SEQUENCE: 4

```
Ser Met Asn Ser Arg Gly Pro Ala Gly Arg Leu Gly Ser Val Pro Thr
  1               5                  10                  15

Ala Lys Leu Ala Asn Gly Asp Thr Ile Thr Gly Leu Asn Ala Ile Ile
             20                  25                  30

Asn Glu Ala Phe Leu Gly Ile Pro Phe Ala Glu Pro Pro Val Gly Asn
         35                  40                  45

Leu Arg Phe Lys Asp Pro Val Pro Tyr Ser Gly Ser Leu Asn Gly Gln
     50                  55                  60

Lys Phe Thr Ser Tyr Gly Pro Ser Cys Met Gln Gln Asn Pro Glu Gly
 65                  70                  75                  80

Thr Phe Glu Glu Asn Leu Gly Lys Thr Ala Leu Asp Leu Val Met Gln
                 85                  90                  95

Ser Lys Val Phe Gln Ala Val Leu Pro Gln Ser Glu Asp Cys Leu Thr
            100                 105                 110

Ile Asn Val Val Arg Pro Pro Gly Thr Lys Ala Gly Ala Asn Leu Pro
        115                 120                 125

Val Met Leu Trp Ile Phe Gly Gly Gly Phe Glu Ile Gly Ser Pro Thr
    130                 135                 140

Ile Phe Pro Pro Ala Gln Met Val Thr Lys Ser Val Leu Met Gly Lys
145                 150                 155                 160

His Ile Ile His Val Ala Val Asn Tyr Arg Val Ala Ser Trp Gly Phe
                165                 170                 175

Leu Ala Gly Asp Asp Ile Lys Ala Glu Gly Ser Gly Asn Ala Gly Leu
            180                 185                 190

Lys Asp Gln Arg Leu Gly Met Gln Trp Val Ala Asp Asn Ile Ala Gly
```

-continued

```
                195                 200                 205
Phe Gly Gly Asp Pro Ser Lys Val Thr Ile Phe Gly Glu Ser Ala Gly
    210                 215                 220

Ser Met Ser Val Leu Cys His Leu Ile Trp Asn Asp Gly Asp Asn Thr
225                 230                 235                 240

Tyr Lys Gly Lys Pro Leu Phe Arg Ala Gly Ile Met Gln Ser Gly Ala
                245                 250                 255

Met Val Pro Ser Asp Pro Val Asp Gly Thr Tyr Gly Asn Glu Ile Tyr
            260                 265                 270

Asp Leu Phe Val Ser Ser Ala Gly Cys Gly Ser Ala Ser Asp Lys Leu
        275                 280                 285

Ala Cys Leu Arg Ser Ala Ser Ser Asp Thr Leu Leu Asp Ala Thr Asn
    290                 295                 300

Asn Thr Pro Gly Phe Leu Ala Tyr Ser Ser Leu Arg Leu Ser Tyr Leu
305                 310                 315                 320

Pro Arg Pro Asp Gly Lys Asn Ile Thr Asp Asp Met Tyr Lys Leu Val
                325                 330                 335

Arg Asp Gly Lys Tyr Ala Ser Val Pro Val Ile Ile Gly Asp Gln Asn
            340                 345                 350

Asp Glu Gly Thr Ile Phe Gly Leu Ser Ser Leu Asn Val Thr Thr Asn
        355                 360                 365

Ala Gln Ala Arg Ala Tyr Phe Lys Gln Ser Phe Ile His Ala Ser Asp
    370                 375                 380

Ala Glu Ile Asp Thr Leu Met Ala Ala Tyr Pro Gln Asp Ile Thr Gln
385                 390                 395                 400

Gly Ser Pro Phe Asp Thr Gly Val Leu Asn Ala Leu Thr Pro Gln Phe
                405                 410                 415

Lys Arg Ile Ser Ala Val Leu Gly Asp Leu Ala Phe Ile His Ala Arg
            420                 425                 430

Arg Tyr Phe Leu Asn His Phe Gln Gly Gly Thr Lys Tyr Ser Phe Leu
        435                 440                 445

Ser Lys Gln Leu Ser Gly Leu Pro Ile Met Gly Thr Phe His Ala Asn
    450                 455                 460

Asp Ile Val Trp Gln Asp Tyr Leu Leu Gly Ser Gly Ser Val Ile Tyr
465                 470                 475                 480

Asn Asn Ala Phe Ile Ala Phe Ala Thr Asp Leu Asp Pro Asn Thr Ala
                485                 490                 495

Gly Leu Leu Val Asn Trp Pro Lys Tyr Thr Ser Ser Gln Ser Gly
            500                 505                 510

Asn Asn Leu Met Met Ile Asn Ala Leu Gly Leu Tyr Thr Gly Lys Asp
        515                 520                 525

Asn Phe Arg Thr Ala Gly Tyr Asp Ala Leu Met Thr Asn Pro Ser Ser
    530                 535                 540

Phe Phe Val
545
```

<210> SEQ ID NO 5
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 5

| | | |
|---|---|---|
| tcg atg aat tca cgt ggc cca gcc ggc cgt ctc gga tcg gta ccc act<br>Ser Met Asn Ser Arg Gly Pro Ala Gly Arg Leu Gly Ser Val Pro Thr<br>1               5                   10                  15 | 48 | |
| gcc acg ctc gcc aac ggc gac acc atc acc ggt ctc aac gcc atc atc<br>Ala Thr Leu Ala Asn Gly Asp Thr Ile Thr Gly Leu Asn Ala Ile Ile<br>        20                  25                  30 | 96 | |
| aac gag gcg ttc ctc ggt att ccc ttt gct cag ccg gtg ggc aac<br>Asn Glu Ala Phe Leu Gly Ile Pro Phe Ala Gln Pro Pro Val Gly Asn<br>    35                  40                  45 | 144 | |
| ctc cgc ttc aag ccg cct gtg ccg tac tcg gcg tct ctc aat ggt cag<br>Leu Arg Phe Lys Pro Pro Val Pro Tyr Ser Ala Ser Leu Asn Gly Gln<br>50                  55                  60 | 192 | |
| aag ttt act tcg tat ggc cct tcg tgc atg cag atg aac cca ttg ggc<br>Lys Phe Thr Ser Tyr Gly Pro Ser Cys Met Gln Met Asn Pro Leu Gly<br>65                  70                  75                  80 | 240 | |
| aac tgg gac tcc tcg ctt ccc aag gct gcc atc aac tcc ttg atg cag<br>Asn Trp Asp Ser Ser Leu Pro Lys Ala Ala Ile Asn Ser Leu Met Gln<br>                85                  90                  95 | 288 | |
| tcc aag ctc ttc cag gcg gtg ctt cct aac ggc gag gac tgt ctc acc<br>Ser Lys Leu Phe Gln Ala Val Leu Pro Asn Gly Glu Asp Cys Leu Thr<br>            100                 105                 110 | 336 | |
| atc aac gtg gtg cgg ccg tca ggc acc aag ccg ggt gcc aac ctc ccc<br>Ile Asn Val Val Arg Pro Ser Gly Thr Lys Pro Gly Ala Asn Leu Pro<br>        115                 120                 125 | 384 | |
| gtg atg gtg tgg att ttt ggc ggc ggg ttt gag gtt ggc ggc tcc agt<br>Val Met Val Trp Ile Phe Gly Gly Gly Phe Glu Val Gly Gly Ser Ser<br>    130                 135                 140 | 432 | |
| ctc ttc cct ccc gca cag atg atc acc gcc agc gtg ctt atg ggc aag<br>Leu Phe Pro Pro Ala Gln Met Ile Thr Ala Ser Val Leu Met Gly Lys<br>145                 150                 155                 160 | 480 | |
| ccc atc atc cac gtg agc atg aac tac cgc gtt gct tcg tgg ggg ttc<br>Pro Ile Ile His Val Ser Met Asn Tyr Arg Val Ala Ser Trp Gly Phe<br>                165                 170                 175 | 528 | |
| ttg gct ggt cca gac atc aag gcc gag ggc agc ggg aac gcc ggt ttg<br>Leu Ala Gly Pro Asp Ile Lys Ala Glu Gly Ser Gly Asn Ala Gly Leu<br>            180                 185                 190 | 576 | |
| cac gac caa cgc ttg ggt ttg cag tgg gtg gcg gac aac att gcc ggg<br>His Asp Gln Arg Leu Gly Leu Gln Trp Val Ala Asp Asn Ile Ala Gly<br>        195                 200                 205 | 624 | |
| ttc ggc ggc gac ccg tcc aag gtg acc atc ttt ggt gag tcg gcg ggc<br>Phe Gly Gly Asp Pro Ser Lys Val Thr Ile Phe Gly Glu Ser Ala Gly<br>    210                 215                 220 | 672 | |
| agc atg tcg gta atg tgt cag ctc ctc tgg aac gac ggc gac aac acg<br>Ser Met Ser Val Met Cys Gln Leu Leu Trp Asn Asp Gly Asp Asn Thr<br>225                 230                 235                 240 | 720 | |
| tac aac ggc aag ccg ttg ttc cgt gcc gcc atc atg cag tct ggg gcc<br>Tyr Asn Gly Lys Pro Leu Phe Arg Ala Ala Ile Met Gln Ser Gly Ala<br>                245                 250                 255 | 768 | |
| atg gtg ccg tcg gac ccg gtg gat ggg ccc tac ggc acg cag atc tac<br>Met Val Pro Ser Asp Pro Val Asp Gly Pro Tyr Gly Thr Gln Ile Tyr<br>            260                 265                 270 | 816 | |
| gac cag gtg gtt gct tca gcc ggc tgt ggc agt gcc agc gac aag ctc<br>Asp Gln Val Val Ala Ser Ala Gly Cys Gly Ser Ala Ser Asp Lys Leu<br>        275                 280                 285 | 864 | |
| gcg tgc ttg cgc agc atc tcg aac gac aaa ctc ttc cag gcc acc agc<br>Ala Cys Leu Arg Ser Ile Ser Asn Asp Lys Leu Phe Gln Ala Thr Ser<br>    290                 295                 300 | 912 | |
| gac act ccg ggg gcc ttg gcg tac ccc tcg ttg cgg ttg tcg ttt ctc<br>Asp Thr Pro Gly Ala Leu Ala Tyr Pro Ser Leu Arg Leu Ser Phe Leu<br>305                 310                 315                 320 | 960 | |

```
ccg cgg ccc gac ggc acc ttc atc acc gat gac atg ttc aag ttg gtg      1008
Pro Arg Pro Asp Gly Thr Phe Ile Thr Asp Asp Met Phe Lys Leu Val
            325                 330                 335 cgc gac ggc aag tgt gcc aac gtt ccg gtg atc att ggc gac cag aac      1056
Arg Asp Gly Lys Cys Ala Asn Val Pro Val Ile Ile Gly Asp Gln Asn
            340                 345                 350 gac gag ggc aca gtg ttt gcg ttg tcc agc ttg aac gtg act acg gat      1104
Asp Glu Gly Thr Val Phe Ala Leu Ser Ser Leu Asn Val Thr Thr Asp
            355                 360                 365 gct cag gca cgc cag tac ttc aag gaa agc ttc atc cac gcc agc gac      1152
Ala Gln Ala Arg Gln Tyr Phe Lys Glu Ser Phe Ile His Ala Ser Asp
370                 375                 380 gcg gag atc gac acc ttg atg gcg gcg tac ccc agc gac atc acc cag      1200
Ala Glu Ile Asp Thr Leu Met Ala Ala Tyr Pro Ser Asp Ile Thr Gln
385                 390                 395                 400 ggt agt ccg ttc gac acc ggc atc ttc aac gcc atc acc ccg cag ttc      1248
Gly Ser Pro Phe Asp Thr Gly Ile Phe Asn Ala Ile Thr Pro Gln Phe
            405                 410                 415 aaa cgg att gca gcg gtg ctt ggt gac ctt gcg ttc act ctc ccc cgg      1296
Lys Arg Ile Ala Ala Val Leu Gly Asp Leu Ala Phe Thr Leu Pro Arg
            420                 425                 430 cgc tac ttc ctc aac cac ttc cag ggc ggc acc aag tac tcg ttc ctc      1344
Arg Tyr Phe Leu Asn His Phe Gln Gly Gly Thr Lys Tyr Ser Phe Leu
            435                 440                 445 tcg aag cag ctt agt ggg ttg ccg gtg att ggc acc cac cac gcc aac      1392
Ser Lys Gln Leu Ser Gly Leu Pro Val Ile Gly Thr His His Ala Asn
450                 455                 460 gac att gtg tgg cag gac ttt ttg gtg agc cac agc agc gcc gtg tac      1440
Asp Ile Val Trp Gln Asp Phe Leu Val Ser His Ser Ser Ala Val Tyr
465                 470                 475                 480 aac aac gcg ttt att gcc ttt gcc aac gac ctc gac ccg aac aag gcc      1488
Asn Asn Ala Phe Ile Ala Phe Ala Asn Asp Leu Asp Pro Asn Lys Ala
                485                 490                 495 ggt ttg ctt gtg aac tgg ccc aag tac acc agc agc tct cag tca ggc      1536
Gly Leu Leu Val Asn Trp Pro Lys Tyr Thr Ser Ser Ser Gln Ser Gly
            500                 505                 510 aac aac ttg ttg cag atc aac gcc ttg ggc ttg tac acc ggc aag gac      1584
Asn Asn Leu Leu Gln Ile Asn Ala Leu Gly Leu Tyr Thr Gly Lys Asp
            515                 520                 525 aac ttc cgc acc gct ggc tac gac gcg ttg ttt acc aac ccg tct tct      1632
Asn Phe Arg Thr Ala Gly Tyr Asp Ala Leu Phe Thr Asn Pro Ser Ser
530                 535                 540 ttc ttt gtg                                                          1641
Phe Phe Val
545

<210> SEQ ID NO 6
<211> LENGTH: 547
<212> TYPE: PRT
<213> ORGANISM: Candida rugosa

<400> SEQUENCE: 6

Ser Met Asn Ser Arg Gly Pro Ala Gly Arg Leu Gly Ser Val Pro Thr
 1               5                  10                  15

Ala Thr Leu Ala Asn Gly Asp Thr Ile Thr Gly Leu Asn Ala Ile Ile
             20                  25                  30

Asn Glu Ala Phe Leu Gly Ile Pro Phe Ala Gln Pro Pro Val Gly Asn
         35                  40                  45

Leu Arg Phe Lys Pro Pro Val Pro Tyr Ser Ala Ser Leu Asn Gly Gln
```

-continued

```
                50                  55                  60
Lys Phe Thr Ser Tyr Gly Pro Ser Cys Met Gln Met Asn Pro Leu Gly
 65                  70                  75                  80

Asn Trp Asp Ser Ser Leu Pro Lys Ala Ala Ile Asn Ser Leu Met Gln
                     85                  90                  95

Ser Lys Leu Phe Gln Ala Val Leu Pro Asn Gly Glu Asp Cys Leu Thr
                100                 105                 110

Ile Asn Val Val Arg Pro Ser Gly Thr Lys Pro Gly Ala Asn Leu Pro
                115                 120                 125

Val Met Val Trp Ile Phe Gly Gly Phe Glu Val Gly Ser Ser
130                 135                 140

Leu Phe Pro Pro Ala Gln Met Ile Thr Ala Ser Val Leu Met Gly Lys
145                 150                 155                 160

Pro Ile Ile His Val Ser Met Asn Tyr Arg Val Ala Ser Trp Gly Phe
                165                 170                 175

Leu Ala Gly Pro Asp Ile Lys Ala Glu Gly Ser Gly Asn Ala Gly Leu
                180                 185                 190

His Asp Gln Arg Leu Gly Leu Gln Trp Val Ala Asp Asn Ile Ala Gly
                195                 200                 205

Phe Gly Gly Asp Pro Ser Lys Val Thr Ile Phe Gly Glu Ser Ala Gly
                210                 215                 220

Ser Met Ser Val Met Cys Gln Leu Leu Trp Asn Asp Gly Asp Asn Thr
225                 230                 235                 240

Tyr Asn Gly Lys Pro Leu Phe Arg Ala Ala Ile Met Gln Ser Gly Ala
                245                 250                 255

Met Val Pro Ser Asp Pro Val Asp Gly Pro Tyr Gly Thr Gln Ile Tyr
                260                 265                 270

Asp Gln Val Val Ala Ser Ala Gly Cys Gly Ser Ala Ser Asp Lys Leu
                275                 280                 285

Ala Cys Leu Arg Ser Ile Ser Asn Asp Lys Leu Phe Gln Ala Thr Ser
                290                 295                 300

Asp Thr Pro Gly Ala Leu Ala Tyr Pro Ser Leu Arg Leu Ser Phe Leu
305                 310                 315                 320

Pro Arg Pro Asp Gly Thr Phe Ile Thr Asp Asp Met Phe Lys Leu Val
                325                 330                 335

Arg Asp Gly Lys Cys Ala Asn Val Pro Val Ile Ile Gly Asp Gln Asn
                340                 345                 350

Asp Glu Gly Thr Val Phe Ala Leu Ser Ser Leu Asn Val Thr Thr Asp
                355                 360                 365

Ala Gln Ala Arg Gln Tyr Phe Lys Glu Ser Phe Ile His Ala Ser Asp
                370                 375                 380

Ala Glu Ile Asp Thr Leu Met Ala Ala Tyr Pro Ser Asp Ile Thr Gln
385                 390                 395                 400

Gly Ser Pro Phe Asp Thr Gly Ile Phe Asn Ala Ile Thr Pro Gln Phe
                405                 410                 415

Lys Arg Ile Ala Ala Val Leu Gly Asp Leu Ala Phe Thr Leu Pro Arg
                420                 425                 430

Arg Tyr Phe Leu Asn His Phe Gln Gly Gly Thr Lys Tyr Ser Phe Leu
                435                 440                 445

Ser Lys Gln Leu Ser Gly Leu Pro Val Ile Gly Thr His His Ala Asn
                450                 455                 460

Asp Ile Val Trp Gln Asp Phe Leu Val Ser His Ser Ser Ala Val Tyr
465                 470                 475                 480
```

```
Asn Asn Ala Phe Ile Ala Phe Ala Asn Asp Leu Asp Pro Asn Lys Ala
            485                 490                 495

Gly Leu Leu Val Asn Trp Pro Lys Tyr Thr Ser Ser Gln Ser Gly
            500                 505             510

Asn Asn Leu Leu Gln Ile Asn Ala Leu Gly Leu Tyr Thr Gly Lys Asp
            515                 520                 525

Asn Phe Arg Thr Ala Gly Tyr Asp Ala Leu Phe Thr Asn Pro Ser Ser
            530                 535                 540

Phe Phe Val
545

<210> SEQ ID NO 7
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 7
```

| | | | | | | | | | | | | | | | | |
|---|---|---|---|---|---|---|---|---|---|---|---|---|---|---|---|---|
| tcg | atg | aat | tca | cgt | ggc | cca | gcc | ggc | cgt | ctc | gga | tcg | gta | ccc | act | 48 |
| Ser | Met | Asn | Ser | Arg | Gly | Pro | Ala | Gly | Arg | Leu | Gly | Ser | Val | Pro | Thr | |
| 1 | | | | 5 | | | | | 10 | | | | | 15 | | |
| gcc | acg | ctc | gcc | aac | ggc | gac | acc | atc | acc | ggt | ctc | aac | gcc | atc | atc | 96 |
| Ala | Thr | Leu | Ala | Asn | Gly | Asp | Thr | Ile | Thr | Gly | Leu | Asn | Ala | Ile | Ile | |
| | | | 20 | | | | | 25 | | | | | 30 | | | |
| aac | gag | gcg | ttc | ctc | ggc | att | ccc | ttt | gcc | gag | ccg | ccg | gtg | ggc | aac | 144 |
| Asn | Glu | Ala | Phe | Leu | Gly | Ile | Pro | Phe | Ala | Glu | Pro | Pro | Val | Gly | Asn | |
| | | 35 | | | | | 40 | | | | | 45 | | | | |
| ctc | cgc | ttc | aag | gac | cct | gtg | ccg | tac | cgt | ggg | tct | ctc | aac | ggt | caa | 192 |
| Leu | Arg | Phe | Lys | Asp | Pro | Val | Pro | Tyr | Arg | Gly | Ser | Leu | Asn | Gly | Gln | |
| | 50 | | | | | 55 | | | | | 60 | | | | | |
| tcc | ttc | acc | gcg | tac | ggt | ccg | tct | tgc | atg | cag | cag | aac | ccc | gag | ggc | 240 |
| Ser | Phe | Thr | Ala | Tyr | Gly | Pro | Ser | Cys | Met | Gln | Gln | Asn | Pro | Glu | Gly | |
| 65 | | | | | 70 | | | | | 75 | | | | | 80 | |
| acc | tac | gag | gag | aac | ctc | ccc | aag | gtg | gcg | ctt | gac | ttg | gtg | atg | cag | 288 |
| Thr | Tyr | Glu | Glu | Asn | Leu | Pro | Lys | Val | Ala | Leu | Asp | Leu | Val | Met | Gln | |
| | | | | 85 | | | | | 90 | | | | | 95 | | |
| tcc | aag | gtg | ttc | cag | gct | gtt | ctc | ccc | aac | agc | gag | gac | tgc | ctc | acc | 336 |
| Ser | Lys | Val | Phe | Gln | Ala | Val | Leu | Pro | Asn | Ser | Glu | Asp | Cys | Leu | Thr | |
| | | | 100 | | | | | 105 | | | | | 110 | | | |
| atc | aac | gtg | gtg | cgg | ccg | ccg | ggc | acc | aag | gcg | ggc | gcc | aac | ctc | ccg | 384 |
| Ile | Asn | Val | Val | Arg | Pro | Pro | Gly | Thr | Lys | Ala | Gly | Ala | Asn | Leu | Pro | |
| | | 115 | | | | | 120 | | | | | 125 | | | | |
| gtc | atg | ctc | tgg | atc | ttt | ggc | ggt | ggg | ttt | gag | atc | ggc | agc | ccc | acc | 432 |
| Val | Met | Leu | Trp | Ile | Phe | Gly | Gly | Gly | Phe | Glu | Ile | Gly | Ser | Pro | Thr | |
| | 130 | | | | | 135 | | | | | 140 | | | | | |
| atc | ttc | cct | ccc | gct | cag | atg | gtc | tcc | aag | agt | gtg | ctc | atg | ggc | gag | 480 |
| Ile | Phe | Pro | Pro | Ala | Gln | Met | Val | Ser | Lys | Ser | Val | Leu | Met | Gly | Glu | |
| 145 | | | | | 150 | | | | | 155 | | | | | 160 | |
| ccc | atc | atc | cac | gtg | gcc | gtc | aac | tac | cgc | ttg | gcg | tcc | ttt | ggt | ttc | 528 |
| Pro | Ile | Ile | His | Val | Ala | Val | Asn | Tyr | Arg | Leu | Ala | Ser | Phe | Gly | Phe | |
| | | | | 165 | | | | | 170 | | | | | 175 | | |
| ttg | gcc | ggt | ccg | gac | atc | aag | gcc | gag | ggc | agc | tcc | aat | gcc | ggc | ctc | 576 |
| Leu | Ala | Gly | Pro | Asp | Ile | Lys | Ala | Glu | Gly | Ser | Ser | Asn | Ala | Gly | Leu | |
| | | | 180 | | | | | 185 | | | | | 190 | | | |
| aag | gac | cag | cgc | ttg | ggc | atg | cag | tgg | gtg | gca | gac | aac | att | gcc | ggg | 624 |
| Lys | Asp | Gln | Arg | Leu | Gly | Met | Gln | Trp | Val | Ala | Asp | Asn | Ile | Ala | Gly | |
| | | 195 | | | | | 200 | | | | | 205 | | | | |

-continued

| | |
|---|---|
| ttc ggc ggc gac ccg agc aag gtg acc atc ttt ggc gag tct gcg ggc<br>Phe Gly Gly Asp Pro Ser Lys Val Thr Ile Phe Gly Glu Ser Ala Gly<br>210                         215                          220 | 672 |
| agc atg tcc gtg ttg tgc cac ctt ctc tgg aat ggc ggc gac aac acg<br>Ser Met Ser Val Leu Cys His Leu Leu Trp Asn Gly Gly Asp Asn Thr<br>225                         230                       235                  240 | 720 |
| tac aag ggc aag ccg ttg ttc cgc gcg ggc atc atg cag tct gga gcc<br>Tyr Lys Gly Lys Pro Leu Phe Arg Ala Gly Ile Met Gln Ser Gly Ala<br>                        245                       250                       255 | 768 |
| atg gtg ccg tct gac ccg gtg gac ggc acc tat gga gcc caa atc tat<br>Met Val Pro Ser Asp Pro Val Asp Gly Thr Tyr Gly Ala Gln Ile Tyr<br>                260                       265                       270 | 816 |
| gac acg ttg gtg gct tct acg ggc tgc agc agt gcc agc aac aag ctt<br>Asp Thr Leu Val Ala Ser Thr Gly Cys Ser Ser Ala Ser Asn Lys Leu<br>        275                       280                       285 | 864 |
| gcg tgc ttg cgt ggt ctt tct act cag gca ttg ctc gat gcc acc aac<br>Ala Cys Leu Arg Gly Leu Ser Thr Gln Ala Leu Leu Asp Ala Thr Asn<br>290                         295                       300 | 912 |
| gac acc cct ggg ttc ttg tcg tac acc tcg ttg cgg ttg tct tat ctc<br>Asp Thr Pro Gly Phe Leu Ser Tyr Thr Ser Leu Arg Leu Ser Tyr Leu<br>305                         310                       315                  320 | 960 |
| ccg cgg ccc gac ggc gcc aac atc acc gat gac atg tac aag ttg gta<br>Pro Arg Pro Asp Gly Ala Asn Ile Thr Asp Asp Met Tyr Lys Leu Val<br>                        325                       330                       335 | 1008 |
| cgc gac ggc aag tat gca agc gtt ccc gtg atc att ggc gac cag aac<br>Arg Asp Gly Lys Tyr Ala Ser Val Pro Val Ile Ile Gly Asp Gln Asn<br>                        340                       345                       350 | 1056 |
| gac gag ggc ttc ttg ttt gat ctc tct tct ttg aac acc acc acc gag<br>Asp Glu Gly Phe Leu Phe Asp Leu Ser Ser Leu Asn Thr Thr Thr Glu<br>                355                       360                       365 | 1104 |
| gcc gac gcc gag gca tac ctc aga aag tct ttc atc cac gcc acc gac<br>Ala Asp Ala Glu Ala Tyr Leu Arg Lys Ser Phe Ile His Ala Thr Asp<br>370                         375                       380 | 1152 |
| gcc gat atc acc gca ttg aag gcg gcg tac ccc agc gat gtc acc cag<br>Ala Asp Ile Thr Ala Leu Lys Ala Ala Tyr Pro Ser Asp Val Thr Gln<br>385                         390                       395                  400 | 1200 |
| ggt tct ccg ttc gac acg ggc att ctc aac gcc ctt aca ccc cag ctc<br>Gly Ser Pro Phe Asp Thr Gly Ile Leu Asn Ala Leu Thr Pro Gln Leu<br>                        405                       410                       415 | 1248 |
| aag cgg atc aat gct gtg ctt ggc gac ctc acc ttt acc ctc tcg cgc<br>Lys Arg Ile Asn Ala Val Leu Gly Asp Leu Thr Phe Thr Leu Ser Arg<br>                        420                       425                       430 | 1296 |
| cgc tac ttc ctc aac cac tac acc ggt ggt ccc aag tac tcg ttc ctc<br>Arg Tyr Phe Leu Asn His Tyr Thr Gly Gly Pro Lys Tyr Ser Phe Leu<br>                435                       440                       445 | 1344 |
| tct aag cag ctt tct ggg ttg ccc att ctc ggt acg ttc cac gcg aac<br>Ser Lys Gln Leu Ser Gly Leu Pro Ile Leu Gly Thr Phe His Ala Asn<br>450                         455                       460 | 1392 |
| gac att gtg tgg cag cac ttt ttg ttg ggc agc ggc agc gtc atc tac<br>Asp Ile Val Trp Gln His Phe Leu Leu Gly Ser Gly Ser Val Ile Tyr<br>465                         470                       475                  480 | 1440 |
| aac aac gcg ttc atc gcg ttt gcc acc gac ttg gac ccc aac acc gcg<br>Asn Asn Ala Phe Ile Ala Phe Ala Thr Asp Leu Asp Pro Asn Thr Ala<br>                        485                       490                       495 | 1488 |
| ggc ttg tct gtg cag tgg ccc aag tac acc agc agc tct cag gcg ggg<br>Gly Leu Ser Val Gln Trp Pro Lys Tyr Thr Ser Ser Ser Gln Ala Gly<br>                  500                       505                       510 | 1536 |
| gac aac ttg atg cag atc agt gcc ttg ggc ttg tac acc ggc aag gac<br>Asp Asn Leu Met Gln Ile Ser Ala Leu Gly Leu Tyr Thr Gly Lys Asp<br>                515                       520                       525 | 1584 |

-continued

```
aac ttc cgc acc gcc ggc tac aac gct ttg ttt gcc gac ccg tct cac    1632
Asn Phe Arg Thr Ala Gly Tyr Asn Ala Leu Phe Ala Asp Pro Ser His
    530                 535                 540 ttt ttc gtg                                                         1641
Phe Phe Val
545
```

<210> SEQ ID NO 8
<211> LENGTH: 547
<212> TYPE: PRT
<213> ORGANISM: Candida rugosa

<400> SEQUENCE: 8

```
Ser Met Asn Ser Arg Gly Pro Ala Gly Arg Leu Gly Ser Val Pro Thr
  1               5                  10                  15

Ala Thr Leu Ala Asn Gly Asp Thr Ile Thr Gly Leu Asn Ala Ile Ile
             20                  25                  30

Asn Glu Ala Phe Leu Gly Ile Pro Phe Ala Glu Pro Pro Val Gly Asn
         35                  40                  45

Leu Arg Phe Lys Asp Pro Val Pro Tyr Arg Gly Ser Leu Asn Gly Gln
     50                  55                  60

Ser Phe Thr Ala Tyr Gly Pro Ser Cys Met Gln Gln Asn Pro Glu Gly
 65                  70                  75                  80

Thr Tyr Glu Glu Asn Leu Pro Lys Val Ala Leu Asp Leu Val Met Gln
                 85                  90                  95

Ser Lys Val Phe Gln Ala Val Leu Pro Asn Ser Glu Asp Cys Leu Thr
            100                 105                 110

Ile Asn Val Val Arg Pro Pro Gly Thr Lys Ala Gly Ala Asn Leu Pro
        115                 120                 125

Val Met Leu Trp Ile Phe Gly Gly Gly Phe Glu Ile Gly Ser Pro Thr
    130                 135                 140

Ile Phe Pro Pro Ala Gln Met Val Ser Lys Ser Val Leu Met Gly Glu
145                 150                 155                 160

Pro Ile Ile His Val Ala Val Asn Tyr Arg Leu Ala Ser Phe Gly Phe
                165                 170                 175

Leu Ala Gly Pro Asp Ile Lys Ala Glu Gly Ser Ser Asn Ala Gly Leu
            180                 185                 190

Lys Asp Gln Arg Leu Gly Met Gln Trp Val Ala Asp Asn Ile Ala Gly
        195                 200                 205

Phe Gly Gly Asp Pro Ser Lys Val Thr Ile Phe Gly Glu Ser Ala Gly
    210                 215                 220

Ser Met Ser Val Leu Cys His Leu Leu Trp Asn Gly Gly Asp Asn Thr
225                 230                 235                 240

Tyr Lys Gly Lys Pro Leu Phe Arg Ala Gly Ile Met Gln Ser Gly Ala
                245                 250                 255

Met Val Pro Ser Asp Pro Val Asp Gly Thr Tyr Gly Ala Gln Ile Tyr
            260                 265                 270

Asp Thr Leu Val Ala Ser Thr Gly Cys Ser Ser Ala Ser Asn Lys Leu
        275                 280                 285

Ala Cys Leu Arg Gly Leu Ser Thr Gln Ala Leu Leu Asp Ala Thr Asn
    290                 295                 300

Asp Thr Pro Gly Phe Leu Ser Tyr Thr Ser Leu Arg Leu Ser Tyr Leu
305                 310                 315                 320

Pro Arg Pro Asp Gly Ala Asn Ile Thr Asp Asp Met Tyr Lys Leu Val
                325                 330                 335
```

```
Arg Asp Gly Lys Tyr Ala Ser Val Pro Val Ile Ile Gly Asp Gln Asn
        340                 345                 350

Asp Glu Gly Phe Leu Phe Asp Leu Ser Ser Leu Asn Thr Thr Thr Glu
        355                 360                 365

Ala Asp Ala Glu Ala Tyr Leu Arg Lys Ser Phe Ile His Ala Thr Asp
        370                 375                 380

Ala Asp Ile Thr Ala Leu Lys Ala Ala Tyr Pro Ser Asp Val Thr Gln
385                 390                 395                 400

Gly Ser Pro Phe Asp Thr Gly Ile Leu Asn Ala Leu Thr Pro Gln Leu
                405                 410                 415

Lys Arg Ile Asn Ala Val Leu Gly Asp Leu Thr Phe Thr Leu Ser Arg
            420                 425                 430

Arg Tyr Phe Leu Asn His Tyr Thr Gly Gly Pro Lys Tyr Ser Phe Leu
        435                 440                 445

Ser Lys Gln Leu Ser Gly Leu Pro Ile Leu Gly Thr Phe His Ala Asn
    450                 455                 460

Asp Ile Val Trp Gln His Phe Leu Leu Gly Ser Gly Ser Val Ile Tyr
465                 470                 475                 480

Asn Asn Ala Phe Ile Ala Phe Ala Thr Asp Leu Asp Pro Asn Thr Ala
                485                 490                 495

Gly Leu Ser Val Gln Trp Pro Lys Tyr Thr Ser Ser Ser Gln Ala Gly
                500                 505                 510

Asp Asn Leu Met Gln Ile Ser Ala Leu Gly Leu Tyr Thr Gly Lys Asp
            515                 520                 525

Asn Phe Arg Thr Ala Gly Tyr Asn Ala Leu Phe Ala Asp Pro Ser His
        530                 535                 540

Phe Phe Val
545

<210> SEQ ID NO 9
<211> LENGTH: 1641
<212> TYPE: DNA
<213> ORGANISM: Candida rugosa
<220> FEATURE:
<221> NAME/KEY: CDS
<222> LOCATION: (1)...(1641)

<400> SEQUENCE: 9 tcg atg aat tca cgt ggc cca gcc ggc cgt ctc gga tcg gta ccc act      48
Ser Met Asn Ser Arg Gly Pro Ala Gly Arg Leu Gly Ser Val Pro Thr
 1               5                  10                  15 gcc acg ctc gcc aac ggc gac acc atc acc ggt ctc aac gcc atc atc      96
Ala Thr Leu Ala Asn Gly Asp Thr Ile Thr Gly Leu Asn Ala Ile Ile
                20                  25                  30 aac gag gcg ttc ctc ggc att ccc ttt gcc gag ccg ccg gtg ggc aac     144
Asn Glu Ala Phe Leu Gly Ile Pro Phe Ala Glu Pro Pro Val Gly Asn
            35                  40                  45 ctc cgc ttc aag gac ccc gtg ccg tac tcc ggc tcg ctc gat ggc cag     192
Leu Arg Phe Lys Asp Pro Val Pro Tyr Ser Gly Ser Leu Asp Gly Gln
        50                  55                  60 aag ttc act tct tac ggc ccg tct tgc atg cag cag aac ccc gag ggc     240
Lys Phe Thr Ser Tyr Gly Pro Ser Cys Met Gln Gln Asn Pro Glu Gly
65                  70                  75                  80 acc tac gag gag aac ctc ccc aag gca gcg ctc gac ttg gtg atg cag     288
Thr Tyr Glu Glu Asn Leu Pro Lys Ala Ala Leu Asp Leu Val Met Gln
                85                  90                  95 tcc aag gtg ttt gag gcg gtg tct ccg tct agc gag gac tgt ctc acc     336
```

-continued

| | | |
|---|---|---|
| Ser Lys Val Phe Glu Ala Val Ser Pro Ser Ser Glu Asp Cys Leu Thr<br>100 105 110 | | |
| atc aac gtg gtg cgg ccg ccg ggc acc aag gcg ggt gcc aac ctc ccg<br>Ile Asn Val Val Arg Pro Pro Gly Thr Lys Ala Gly Ala Asn Leu Pro<br>115 120 125 | 384 | |
| gtg atg ctc tgg atc ttt ggc ggc ggg ttt gag gtg ggt ggc acc agc<br>Val Met Leu Trp Ile Phe Gly Gly Gly Phe Glu Val Gly Gly Thr Ser<br>130 135 140 | 432 | |
| acc ttc cct ccc gcc cag atg atc acc aag agc att gcc atg ggc aag<br>Thr Phe Pro Pro Ala Gln Met Ile Thr Lys Ser Ile Ala Met Gly Lys<br>145 150 155 160 | 480 | |
| ccc atc atc cac gtg agc gtc aac tac cgc gtg tcg tcg tgg ggg ttc<br>Pro Ile Ile His Val Ser Val Asn Tyr Arg Val Ser Ser Trp Gly Phe<br>165 170 175 | 528 | |
| ttg gct ggc gac gag atc aag gcc gag ggc agt gcc aac gcc ggt ttg<br>Leu Ala Gly Asp Glu Ile Lys Ala Glu Gly Ser Ala Asn Ala Gly Leu<br>180 185 190 | 576 | |
| aag gac cag cgc atg ggc atg cag tgg gtg gcg gac aac att gcg gcg<br>Lys Asp Gln Arg Met Gly Met Gln Trp Val Ala Asp Asn Ile Ala Ala<br>195 200 205 | 624 | |
| ttt ggc ggc gac ccg acc aag gtg acc atc ttt ggc gag tct gcg ggc<br>Phe Gly Gly Asp Pro Thr Lys Val Thr Ile Phe Gly Glu Ser Ala Gly<br>210 215 220 | 672 | |
| agc atg tcg gtc atg tgc cac att ctc tgg aac gac ggc gac aac acg<br>Ser Met Ser Val Met Cys His Ile Leu Trp Asn Asp Gly Asp Asn Thr<br>225 230 235 240 | 720 | |
| tac aag ggc aag ccg ctc ttc cgc gcg ggc atc atg cag tct ggg gcc<br>Tyr Lys Gly Lys Pro Leu Phe Arg Ala Gly Ile Met Gln Ser Gly Ala<br>245 250 255 | 768 | |
| atg gta ccg tcg gac gcg gtg gac ggc gtc tac ggc aac gag atc ttt<br>Met Val Pro Ser Asp Ala Val Asp Gly Val Tyr Gly Asn Glu Ile Phe<br>260 265 270 | 816 | |
| gac ctc ttg gcg tcg gac gcg ggc tgc ggc agc gcc agc gac aag ctt<br>Asp Leu Leu Ala Ser Asp Ala Gly Cys Gly Ser Ala Ser Asp Lys Leu<br>275 280 285 | 864 | |
| gcg tgc ttg cgc ggt gtg tct agc gac acg ttg gag gac gcc acc aac<br>Ala Cys Leu Arg Gly Val Ser Ser Asp Thr Leu Glu Asp Ala Thr Asn<br>290 295 300 | 912 | |
| aac acc cct ggg ttc ttg gcg tac tcc tcg ttg cgg ttg tct tat ctc<br>Asn Thr Pro Gly Phe Leu Ala Tyr Ser Ser Leu Arg Leu Ser Tyr Leu<br>305 310 315 320 | 960 | |
| ccg cgg ccc gac ggc gtg aac atc acc gac gac atg ttt gcc ttg gtc<br>Pro Arg Pro Asp Gly Val Asn Ile Thr Asp Asp Met Phe Ala Leu Val<br>325 330 335 | 1008 | |
| cgc gag ggc aag tat gca agc gtt cct gtg atc atc ggc gac cag aac<br>Arg Glu Gly Lys Tyr Ala Ser Val Pro Val Ile Ile Gly Asp Gln Asn<br>340 345 350 | 1056 | |
| gac gag ggc acc ttc ttt ggc acc tct tct ttg aac gtg acc acg gat<br>Asp Glu Gly Thr Phe Phe Gly Thr Ser Ser Leu Asn Val Thr Thr Asp<br>355 360 365 | 1104 | |
| gcc gag gcc cgc cag tac ttc acg cag tct ttt gtc cac gcc agc gac<br>Ala Glu Ala Arg Gln Tyr Phe Thr Gln Ser Phe Val His Ala Ser Asp<br>370 375 380 | 1152 | |
| gcg gag ctc gac acg ttg atg acg gcg tac ccc cag gac atc acc cag<br>Ala Glu Leu Asp Thr Leu Met Thr Ala Tyr Pro Gln Asp Ile Thr Gln<br>385 390 395 400 | 1200 | |
| ggt tct ccg ttc gac acg ggt gtt ctc aac gcc ctc acc ccg cag ttc<br>Gly Ser Pro Phe Asp Thr Gly Val Leu Asn Ala Leu Thr Pro Gln Phe<br>405 410 415 | 1248 | |

-continued

```
aag aga atc tct gcg gtg ctc ggc gac ctt gcc ttc atc cac gcc cgt    1296
Lys Arg Ile Ser Ala Val Leu Gly Asp Leu Ala Phe Ile His Ala Arg
        420                 425                 430 cgc tac ttc ctc aac cac tac acc ggc ggc acc aag tac tca ttc ctc    1344
Arg Tyr Phe Leu Asn His Tyr Thr Gly Gly Thr Lys Tyr Ser Phe Leu
    435                 440                 445 tct aag cag ctc tct ggc ttg ccg gtg ctc gga acg ttc cac tcc aac    1392
Ser Lys Gln Leu Ser Gly Leu Pro Val Leu Gly Thr Phe His Ser Asn
450                 455                 460 gac att gtc ttc cag gac tac ttg ttg ggc agc ggc tcg ctc atc tac    1440
Asp Ile Val Phe Gln Asp Tyr Leu Leu Gly Ser Gly Ser Leu Ile Tyr
465                 470                 475                 480 aac aac gcg ttc att gcg ttt gcc acg gac ttg gac ccc aac acc gcg    1488
Asn Asn Ala Phe Ile Ala Phe Ala Thr Asp Leu Asp Pro Asn Thr Ala
                485                 490                 495 ggg ttg ttg gtg aag tgg ccc gag tac acc agc agc tct cag tct ggc    1536
Gly Leu Leu Val Lys Trp Pro Glu Tyr Thr Ser Ser Ser Gln Ser Gly
            500                 505                 510 aac aac ttg atg atg atc aac gcc ttg ggc ttg tac acc ggc aag gac    1584
Asn Asn Leu Met Met Ile Asn Ala Leu Gly Leu Tyr Thr Gly Lys Asp
        515                 520                 525 aac tcc cgc acc gcc ggc tac gac gcg ttg ttc tcc aac ccg ccg tct    1632
Asn Ser Arg Thr Ala Gly Tyr Asp Ala Leu Phe Ser Asn Pro Pro Ser
530                 535                 540 ttc ttt gtg                                                         1641
Phe Phe Val
545

<210> SEQ ID NO 10
<211> LENGTH: 547
<212> TYPE: PRT
<213> ORGANISM: Candida rugosa

<400> SEQUENCE: 10

Ser Met Asn Ser Arg Gly Pro Ala Gly Arg Leu Gly Ser Val Pro Thr
 1               5                  10                  15

Ala Thr Leu Ala Asn Gly Asp Thr Ile Thr Gly Leu Asn Ala Ile Ile
            20                  25                  30

Asn Glu Ala Phe Leu Gly Ile Pro Phe Ala Glu Pro Pro Val Gly Asn
        35                  40                  45

Leu Arg Phe Lys Asp Pro Val Pro Tyr Ser Gly Ser Leu Asp Gly Gln
    50                  55                  60

Lys Phe Thr Ser Tyr Gly Pro Ser Cys Met Gln Gln Asn Pro Glu Gly
65                  70                  75                  80

Thr Tyr Glu Glu Asn Leu Pro Lys Ala Ala Leu Asp Leu Val Met Gln
                85                  90                  95

Ser Lys Val Phe Glu Ala Val Ser Pro Ser Ser Glu Asp Cys Leu Thr
            100                 105                 110

Ile Asn Val Val Arg Pro Pro Gly Thr Lys Ala Gly Ala Asn Leu Pro
        115                 120                 125

Val Met Leu Trp Ile Phe Gly Gly Gly Phe Glu Val Gly Gly Thr Ser
    130                 135                 140

Thr Phe Pro Pro Ala Gln Met Ile Thr Lys Ser Ile Ala Met Gly Lys
145                 150                 155                 160

Pro Ile Ile His Val Ser Val Asn Tyr Arg Val Ser Ser Trp Gly Phe
                165                 170                 175
```

```
Leu Ala Gly Asp Glu Ile Lys Ala Glu Gly Ser Ala Asn Ala Gly Leu
            180                 185                 190

Lys Asp Gln Arg Met Gly Met Gln Trp Val Ala Asp Asn Ile Ala Ala
            195                 200                 205

Phe Gly Gly Asp Pro Thr Lys Val Thr Ile Phe Gly Glu Ser Ala Gly
            210                 215                 220

Ser Met Ser Val Met Cys His Ile Leu Trp Asn Asp Gly Asp Asn Thr
225                 230                 235                 240

Tyr Lys Gly Lys Pro Leu Phe Arg Ala Gly Ile Met Gln Ser Gly Ala
            245                 250                 255

Met Val Pro Ser Asp Ala Val Asp Gly Val Tyr Gly Asn Glu Ile Phe
            260                 265                 270

Asp Leu Leu Ala Ser Asp Ala Gly Cys Gly Ser Ala Ser Asp Lys Leu
            275                 280                 285

Ala Cys Leu Arg Gly Val Ser Ser Asp Thr Leu Glu Asp Ala Thr Asn
            290                 295                 300

Asn Thr Pro Gly Phe Leu Ala Tyr Ser Ser Leu Arg Leu Ser Tyr Leu
305                 310                 315                 320

Pro Arg Pro Asp Gly Val Asn Ile Thr Asp Asp Met Phe Ala Leu Val
            325                 330                 335

Arg Glu Gly Lys Tyr Ala Ser Val Pro Val Ile Ile Gly Asp Gln Asn
            340                 345                 350

Asp Glu Gly Thr Phe Phe Gly Thr Ser Ser Leu Asn Val Thr Thr Asp
            355                 360                 365

Ala Glu Ala Arg Gln Tyr Phe Thr Gln Ser Phe Val His Ala Ser Asp
            370                 375                 380

Ala Glu Leu Asp Thr Leu Met Thr Ala Tyr Pro Gln Asp Ile Thr Gln
385                 390                 395                 400

Gly Ser Pro Phe Asp Thr Gly Val Leu Asn Ala Leu Thr Pro Gln Phe
            405                 410                 415

Lys Arg Ile Ser Ala Val Leu Gly Asp Leu Ala Phe Ile His Ala Arg
            420                 425                 430

Arg Tyr Phe Leu Asn His Tyr Thr Gly Gly Thr Lys Tyr Ser Phe Leu
            435                 440                 445

Ser Lys Gln Leu Ser Gly Leu Pro Val Leu Gly Thr Phe His Ser Asn
450                 455                 460

Asp Ile Val Phe Gln Asp Tyr Leu Leu Gly Ser Gly Ser Leu Ile Tyr
465                 470                 475                 480

Asn Asn Ala Phe Ile Ala Phe Ala Thr Asp Leu Asp Pro Asn Thr Ala
            485                 490                 495

Gly Leu Leu Val Lys Trp Pro Glu Tyr Thr Ser Ser Ser Gln Ser Gly
            500                 505                 510

Asn Asn Leu Met Met Ile Asn Ala Leu Gly Leu Tyr Thr Gly Lys Asp
            515                 520                 525

Asn Ser Arg Thr Ala Gly Tyr Asp Ala Leu Phe Ser Asn Pro Pro Ser
530                 535                 540

Phe Phe Val
545
```

```
<210> SEQ ID NO 11
<211> LENGTH: 13
<212> TYPE: PRT
<213> ORGANISM: Candida rugosa

<400> SEQUENCE: 11

Ser Met Asn Ser Arg Gly Pro Ala Gly Arg Leu Gly Ser
1               5                   10
```